United States Patent
Jiang et al.

(10) Patent No.: US 7,074,824 B2
(45) Date of Patent: Jul. 11, 2006

(54) PHARMACEUTICAL COMPOSITIONS CONTAINING BETA-LAPACHONE, OR DERIVATIVES OR ANALOGS THEREOF, AND METHODS OF USING SAME

(75) Inventors: Zhiwei Jiang, Grafton, MA (US); Dasharatha G. Reddy, Acton, MA (US)

(73) Assignee: Arqule, Inc., Woburn, MA (US)

( * ) Notice: Subject to any disclaimer, the term of this patent is extended or adjusted under 35 U.S.C. 154(b) by 260 days.

(21) Appl. No.: 10/343,091

(22) PCT Filed: Jul. 31, 2002

(86) PCT No.: PCT/US02/24262
§ 371 (c)(1),
(2), (4) Date: Jan. 27, 2003

(87) PCT Pub. No.: WO03/011224
PCT Pub. Date: Feb. 13, 2003

(65) Prior Publication Data
US 2004/0071775 A1    Apr. 15, 2004

Related U.S. Application Data

(63) Continuation-in-part of application No. 09/975,776, filed on Oct. 10, 2001, now Pat. No. 6,962,944.
(60) Provisional application No. 60/308,935, filed on Jul. 31, 2001.

(51) Int. Cl.
*A01N 43/16* (2006.01)
*A06N 31/35* (2006.01)

(52) U.S. Cl. ............ 514/455; 514/454; 514/461; 514/777; 514/937; 514/941; 514/970

(58) Field of Classification Search ............ 514/454, 514/455, 461, 777, 937, 941, 970
See application file for complete search history.

(56) References Cited

U.S. PATENT DOCUMENTS
2,827,452 A    3/1958    Schlenk
(Continued)

FOREIGN PATENT DOCUMENTS
DE    33 45 780.8    12/1983
(Continued)

OTHER PUBLICATIONS

Stella VJ and Rajewski RA. "Cyclodextrins: their future in drug formulation," 1997 Pharmaceutical Research 14(5): 556-567.*
(Continued)

*Primary Examiner*—Raymond Henley, III
*Assistant Examiner*—Amy Lewis
(74) *Attorney, Agent, or Firm*—Mintz, Levin, Cohn, Ferris, Glovsky and Popeo, P.C.; Ivor R. Elrifi; Matthew Pavao

(57) ABSTRACT

Beta-lapachone, which is poorly soluble in most pharmaceutically acceptable solvents, has demonstrated significant antineoplastic activity against human cancer lines. The present invention overcomes this significant limitation by teaching novel pharmaceutical compositions comprising a therapeutically effective amount of Beta-lapachone, or a derivative or analog thereof, and a pharmaceutically acceptable solubilizing carrier molecule, which may be at water-solubilizing carrier molecule such as hydroxypropyl-β-cyclodextrin, or an oil-based solubilizing carrier molecule, for enhancing the solubility of Beta-lapachone in aqueous solution. The therapeutically effective amount of Beta-lapachone, or a derivative or analog thereof, may be complexed with the pharmaceutically acceptable solubilizing carrier molecule in aqueous solution. The novel pharmaceutical compositions may be administered with a second anticancer agent or in combination with radiation therapy. A formulation of Beta-lapachone or a derivative or analog thereof, complexed with a pharmaceutically acceptable solubilizing carrier molecule, wherein the complex can be freeze-dried and when subsequently reconstituted in aqueous solution is substantially soluble is also disclosed. Emulsions of Beta-Lapachone in a pharmaceutically acceptable fat emulsion vehicle are also provided. Also disclosed are methods for treating cancer by administering to a patient the novel pharmaceutical compositions and formulations. Pharmaceutical kits are also provided.

34 Claims, 17 Drawing Sheets

U.S. PATENT DOCUMENTS

| | | | |
|---|---|---|---|
| 3,453,259 | A | 7/1969 | Parmerter et al. |
| 3,459,731 | A | 8/1969 | Gramera et al. |
| 4,371,673 | A | 2/1983 | Pitha |
| 4,380,626 | A | 4/1983 | Szejtli et al. |
| 4,383,992 | A | 5/1983 | Lipari |
| 4,524,068 | A | 6/1985 | Szejtli et al. |
| 4,542,211 | A | 9/1985 | Szejtli et al. |
| 4,555,504 | A | 11/1985 | Jones |
| 4,582,900 | A | 4/1986 | Brandt et al. |
| 4,596,795 | A | 6/1986 | Pitha |
| 4,638,058 | A | 1/1987 | Brandt et al. |
| 4,727,064 | A | 2/1988 | Pitha |
| 5,024,998 | A * | 6/1991 | Bodor .................. 424/1.85 |
| 5,763,625 | A | 6/1998 | Boothman et al. |
| 5,824,700 | A | 10/1998 | Frydman et al. |
| 5,969,163 | A | 10/1999 | Frydman et al. |
| 6,245,807 | B1 | 6/2001 | Pardee et al. |
| 6,407,079 | B1 | 6/2002 | Muller et al. |
| 6,448,030 | B1 * | 9/2002 | Rust et al. .................. 435/29 |
| 6,670,330 | B1 * | 12/2003 | Lampidis et al. ............. 514/23 |

FOREIGN PATENT DOCUMENTS

| | | | |
|---|---|---|---|
| DE | 33 46 123.6 | | 12/1983 |
| EP | 0184990 | | 6/1986 |
| EP | 0 149 197 | | 3/1990 |
| EP | 0 119 543 | | 6/1990 |
| FR | 2 484 252 | | 12/1981 |
| JP | 57126802 | | 8/1982 |
| JP | 57200361 | | 12/1982 |
| JP | 58144376 | | 8/1983 |
| WO | WO 82/00251 | | 2/1982 |
| WO | WO 85/02767 | | 7/1985 |
| WO | WO 94/04145 | | 3/1994 |
| WO | WO 96/11005 | | 4/1996 |
| WO | WO 97/31936 | | 9/1997 |
| WO | WO 00/61142 | * | 4/1999 |
| WO | WO 00/61142 | | 10/2000 |
| WO | WO 01/64214 | | 9/2001 |
| WO | WO 03/090710 | | 11/2003 |

OTHER PUBLICATIONS

Planchon, et al. (1996). *Cancer Res.* 55: 3706-3711.
Li, et al. (1995). *Cancer Res.* 55: 3712-3715.
Weller, et al. (1997). *Int. J. Cancer* 73: 707-714.
Lai, et al. (1998). *Histol. Histopathol.* 13: 89-97.
Huang, et al. (1999). *Mol. Med.* 5: 711-720.
Wuerzberger, et al. (1998). *Cancer Res.* 58: 1876-1885.
Li, et al. (1999). *Proc. Natl. Acad. Sci. USA* 96(23): 13369-13374.
Li, et al. (2000). *Mol. Med.* 6: 1008-1015.
Li, et al. (1999). *Mol. Med.* 5: 232-239.
Boothman, et al. (1987). *Cancer Res.* 47: 5361-5366.
Boorstein and Pardee (1983). *Biochem Biophys. Commun.* 117(1): 30-36.
Schaffner-Sabba, et al. (1984). *J. Med. Chem.* 27: 990-994.
Sun, et al. (1998). *Tetrahedron Letters* 39: 8221-8224.
Amaral, et al. (1992). *J. Heterocyclic Chem.* 29(6): 1457-1460.
Li, et al. (1993). *J. Biol. Chem.* 268(30): 22463-22468.
Portela and Stoppani (1996). *Biochem Pharm* 51: 275-283.
Goncalves, et al. (1980). *Mol. and Biochem Parasitology* 1: 167-176.
Frydman, et al. (1997). *Cancer Res.* 57: 620-627.
Krishnan and Bastow (2000). *Biochem Pharm* 60: 1367-1379.
Pink, et al. (2000). *J. Biol. Chem.* 275(8): 5416-.
Maruyama and Naruta. (1977). *Chem Lett.* pp. 847-850.
Szejtil (1982). Chinoin Res Cent Biochem Res Lab, Budapest, Hungary: 204-232.
Croft and Bartsch (1983). Tetrahedron 39: 1417-1474.
Fenyvesi, et al. (1981). Int Symp Cyclodextrins, Budapest, Hungary: 345-356.
Szejtli, et al. (1980). Starch 32: 165-169.
Nasongkla et al., Pharm Res. 20(10):1626-1633, 2003.
Stella and Rajewski, Pharm Res. 14(5):556-567, 1997.
Szejtli, Chem Rev. 98(5):1743-1754, 1998.
Loftsson and Brewster, J Pharm Sci. 85(10):1017-1025, 1996.
Rajewski and Stella, J Pharm Sci. 85(11):1142-1169, 1996.
Irie and Uekama, J Pharm Sci. 86(2):147-162, 1997.
Rekharsky and Inoue, Chem Rev. 98(5):1875-1918, 1998.
Wuerzberger et al., Cancer Res. 58(9):1876-1885, 1998.
Tagliarino et al., J Biol Chem. 276(22):19150-19159, 2001.

* cited by examiner

| Cell Line | Tissue Origins | Applied drug conc., μM | | Colonies, percentage of control | | |
|---|---|---|---|---|---|---|
| | | β-Lapachone | Taxol | β-Lapachone | Taxol | β-Lapachone + Taxol |
| A2780DDP | Ovary | 2 | 0.2 | 77 (1.1) | 39 (0.8) | 0 |
| MCF-7 | Breast | 4 | 0.1 | 46 (1.4) | 45 (0.3) | 0 |
| 21MT | Breast | 4 | 0.1 | 56 (5.0) | 63 (7.0) | 0 |
| Skmel-28 | Melanoma | 4 | 0.1 | 56 (1.4) | 44 (5.1) | 0 |
| HT-29 | Colon | 4 | 0.1 | 42 (1.4) | 64 (2.5) | 0 |
| ASPC-1 | Pancreas | 4 | 0.2 | 45 (1.9) | 71 (0.8) | 0 |
| G480 | Lung | 4 | 0.2 | 32 (0.3) | 39 (2.6) | 2 (0.1) |
| DU145 | Prostate | 4 | 0.2 | 50 (2.2) | 30 (0.9) | 0 |

Fig. 4

| β-Lap/Taxol Ratio, % IC$_{50}$ | OVCAR-3 Cell Line | | MDAH 2774 Cell Line | |
|---|---|---|---|---|
| | % Absorbance | Significance* | % Absorbance | Significance* |
| 0/0 | 100 | | 100 | |
| 100/0 | 61.2 | | 51.2 | |
| 75/25 | 57.6 | $p < 0.05$ | 30.5 | $p < 0.05$ |
| 60/40 | 59.2 | | 32.0 | $p < 0.05$ |
| 50/50 | 54.9 | $p < 0.05$ | 36.2 | $p < 0.05$ |
| 40/60 | 54.3 | $p < 0.05$ | 35.6 | $p < 0.05$ |
| 25/75 | 55.8 | | 39.2 | $p < 0.05$ |
| 0/100 | 71.0 | | 52.6 | |

Fig. 5

3-bromo-β-lapachone
(MW 321)
(CO-502)

4-hydroxy-β-lapachone
(MW 258)
(CO-503)

4-acetoxy-β-lapachone
(MW 300)
(CO-504)

4-keto-β-lapachone
(MW 256)
(CO-505)

Dunnione Analog
(MW 242)
(CO-506)

4-hexanoyl-1,2-
naphthoquinone
(MW 272)
(CO-507)

3-hydroxy-β-lapachone
(MW 258)

3-(3-methyl-2-butenyl)-
4-methyl-β-lapachone 2-ethyl-6-hydroxynaptho
[2,3-b]-furan-4,5-dione

PHARMACEUTICAL COMPOSITIONS CONTAINING BETA-LAPACHONE, OR DERIVATIVES OR ANALOGS THEREOF, AND METHODS OF USING SAME

RELATED APPLICATION

This application is a National Phase Application which claims priority from PCT/US02/24262, filed Jul. 31, 2002; which is a continuation-in-part of and claims priority from U.S. Ser. No. 09/975,776, filed Oct. 10, 2001; now U.S. Pat. No. 6,962,944 which claims priority from U.S. Ser. No. 60/308,935 filed Jul. 31, 2001, each of which is incorporated by reference in its entirety.

FIELD OF THE INVENTION

The present invention is directed to pharmaceutical compositions and formulations, as well as methods of administering these pharmaceutical compositions and formulations, which comprise β-lapachone (Beta-lapachone), or a derivative or analog thereof, complexed or combined with a solubilizing carrier molecule for enhancing the solubility of β-lapachone in different solvent systems.

BACKGROUND OF THE INVENTION

Over 1.22 million new cancer cases will be diagnosed in the U.S. in the year 2001 alone. With more than 563,000 deaths annually, cancer is the second leading cause of death behind heart disease (UBS Warburg "Disease Dynamics: The Cancer Market", Nov. 8, 2000). Surgery and radiotherapy may be curative if the disease is found early, but current drug therapies for metastatic disease are mostly palliative and seldom offer a long-term cure. Even with the new chemotherapies entering the market, improvement in patient survival is measured in months rather than in years, and the need continues for new drugs effective both in combination with existing agents as first line therapy and as second and third line therapies in treatment of resistant tumors.

In the past, the most successful drug treatment regimens have combined two or more agents, each of which has a different mechanism of action and each of which has anti-tumor activity when used individually. Even though their mechanisms of action differ, most of the agents currently used for chemotherapy of cancer, including alkylating agents, platinum analogs, anthracyclines and the camptothecin family of topoisomerase inhibitors, have in common the property of severely damaging DNA, hence their designation as "DNA-damaging agents". Radiotherapy works similarly. Most DNA-damaging agents as well as the microtubule-targeting agents (e.g., paclitaxel) cause the arrest of cells at the $G_2/M$ transition phase of the cell cycle, a major cell cycle checkpoint where cells make a commitment to repair DNA or to undergo apoptosis if DNA damage al., Molecular and Biochemical Parasitology 1:167–176 (1998) (substituents at the 2- and 3-positions)).

As a single agent, β-lapachone has demonstrated significant antineoplastic activity against human cancer cell lines at concentrations typically in the range of 1-10 μM ($IC_{50}$). Cytotoxicity has been demonstrated in transformed cell lines derived from patients with promyelocytic leukemia (Planchon et al., Cancer Res., 55 (1996) 3706), prostate (Li, C. J., et al., Cancer Res., 55 (1995) 3712), malignant glioma (Weller, M. et al., Int. J. Cancer, 73 (1997) 707), hepatoma (Lai, C. C., et al., Histol Histopathol, 13 (1998) 8), colon (Huang, L., et al., Mol Med, 5, (1999) 711), breast (Wuertzberger, S. M., et al., Cancer Res., 58 (1998) 1876), ovarian (Li, C. J. et al., Proc. Natl. Acad. Sci. USA, 96(23) (1999) 13369-74), pancreatic (Li, Y., et al., Mol Med, 6 (2000) 1008; Li, Y. Z., Mol Med, 5 (1999) 232), and multiple myeloma cell lines, including drug-resistant lines (Li, Y., Mol Med, 6 (2000) 1008). No cytotoxic effects were observed on normal fresh or proliferating human PBMC (Li, Y., Mol Med, 6 (2000) 1008).

β-lapachone has been shown to be a DNA repair inhibitor that sensitizes cells to DNA-damaging agents including radiation (Boothman, D. A. et al., Cancer Res, 47 (1987) 5361; Boorstein, R. J., et al., Biochem. Biophys. Commun., 117 (1983) 30). Although its exact intracellular target(s) and mechanism of cell killing remain unknown, β-lapachone has also shown potent in vitro inhibition of human DNA Topoisomerases I (Li, C. J. et al., J. Biol. Chem., 268 (1993) 22463) and II (Frydman, B. et al., Cancer Res. 57 (1997) 620) with novel mechanisms of action. Unlike topoisomerase "poisons" (e.g., camptothecin, etoposide, doxorubicin) which stabilize the covalent topoisomerase-DNA complex and induce topoisomerase-mediated DNA cleavage, β-lapachone interacts directly with the enzyme to inhibit catalysis and block the formation of cleavable complex (Li, C. J. et al., J. Biol. Chem., 268 (1993) 22463) or with the complex itself, causing religation of DNA breaks and dissociation of the enzyme from DNA (Krishnan, P. et al., Biochem Pharm, 60 (2000) 1367). β-lapachone and its derivatives have also been synthesized and tested as anti-viral and anti-parasitic agents (Goncalves, A. M., et al., Mol. Biochem. Parasitology, 1 (1980) 167–176; Schaffner-Sabba, K., et al., J. Med Chem., 27 (1984) 990–994).

More specifically, β-lapachone appears to work by disrupting DNA replication, causing cell-cycle delays in G1 and/or S phase, inducing either apoptotic or necrotic cell death in a wide variety of human carcinoma cell lines without DNA damage and independent of p53 status (Li, Y. Z. et al (1999); Huang, L. et al.). Topoisomerase I is an enzyme that unwinds the DNA that makes up the chromosomes. The chromosomes must be unwound in order for the cell to use the genetic information to synthesize proteins; β-lapachone keeps the chromosomes wound tight, so that the cell cannot make proteins. As a result, the cell stops growing. Because cancer cells are constantly replicating and circumvent many mechanisms that restrict replication in normal cells, they are more vulnerable to topoisomerase inhibition than are normal cells.

Another possible intracellular target for β-lapachone in tumor cells is the enzyme NAP(P)H:quinone oxidoreductase (NQO1). Biochemical studies suggest that reduction of β-lapachone by NQO1 leads to a "futile cycling" between the quinone and hydroquinone forms with a concomitant loss of reduced NADH or NAD(P)H (Pink, J. J. et al., J. Biol Chem., 275 (2000) 5416). The exhaustion of these reduced enzyme cofactors may be a critical factor for the activation of the apoptotic pathway after β-lapachone treatment.

As a result of these findings, β-lapachone is actively being developed for the treatment of cancer and tumors. In WO00/61142, for example, there is disclosed a method and composition for the treatment of cancer, which comprises the administration of an effective amount of a first compound, a G1 or S phase drug, such as a β-lapachone, in combination with a G2/M drug, such as a taxane derivative. Additionally, U.S. Pat. No. 6,245,807 discloses the use of β-lapachone, amongst other β-lapachone derivatives, for use in the treatment of human prostate disease.

One obstacle, however, to the development of pharmaceutical formulations comprising β-lapachone for parenteral and topical administration is the low solubility of β-lapachone in pharmaceutically acceptable solvents. β-lapachone is highly insoluble in water and has only limited solubility in common solvent systems used for topical and parenteral administration, specifically for intravenous and cutaneous delivery of drugs. As a result, there is a need for improved formulations of β-lapachone for parenteral and topical administration, which are both safe and readily bioavailable to the subject to which the formulation is administered.

SUMMARY OF THE INVENTION

The present invention is directed generally to pharmaceutical compositions containing β-lapachone for use in the treatment of mammalian cancers and which overcome the disadvantages and obstacles of prior art compositions. More specifically, the invention is directed to pharmaceutical compositions containing β-lapachone, or a derivative or analog thereof, and a pharmaceutically acceptable solubilizing carrier molecule for use in the treatment of mammalian cancers, including lung, breast, colon, ovarian and prostate cancers, multiple myeloma, malignant melanoma, non-melanoma skin cancers, as well as proliferation disorders and dermatological conditions such as psoriasis. The pharmaceutical composition may be complexed or combined with the pharmaceutically acceptable solubilizing carrier molecule to form a unitary composition or an inclusion complex. The pharmaceutically acceptable solubilizing carrier molecule is advantageously a water-solubilizing carrier molecule or an oil-based solubilizing carrier molecule.

The present invention provides pharmaceutical compositions of β-lapachone, or a derivative or analog thereof, and a pharmaceutically acceptable solubilizing carrier molecule that enhances the solubility of the β-lapachone and renders it bioavailable in mammalian bodies and suitable for parenteral and topical administration. The concentration of β-lapachone in solution is preferably at least 1 mg/ml, more preferably at least 3 mg/ml, even more preferably at least 5 mg/ml. For concentrated pharmaceutical compositions, we contemplate concentrations of β-lapachone of 10 mg/ml or greater.

The present invention also provides pharmaceutical compositions containing β-lapachone and pharmaceutically acceptable solubilizing carrier molecules in combination with a taxane derivative or other anticancer agent, for use in the treatment of mammalian cancers.

The present invention also provides formulations of β-lapachone, or a derivative or analog thereof, complexed with pharmaceutically acceptable solubilizing carrier molecules, wherein the complex can be freeze-dried and when subsequently reconstituted in aqueous solution is substantially soluble.

The present invention further provides methods for treating mammalian cancers by administering to a patient the pharmaceutical compositions and formulations of the present invention.

The present invention further provides methods for treating cancer and for treating dermatologic conditions by administering to a patient afflicted with cancer or a dermatologic condition, an analog or derivative of β-lapachone, such as 4-aceotoxy-β-lapachone or 4-acetoxy-3-bromo-β-lapachone.

The present invention also provides pharmaceutical kits which comprise one or more containers containing a pharmaceutical composition comprising a therapeutically effective amount of β-lapachone, or a derivative or analog thereof. Such kits may include, if desired, one or more of various conventional pharmaceutical kit components, such as, for example, containers with one or more pharmaceutically acceptable carriers, additional containers, etc. Printed instructions, either as inserts or as labels, indicating quantities of the components to be administered, guidelines for administration, and/or guidelines for mixing the components, may also be included in the kit.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE DRAWINGS

The invention will be better understood by reference to the appended figures in which:

FIG. 4 is a chart illustrating the inhibition of cancer cell survival by β-lapachone and Taxol®;

FIG. 5 is a chart showing the growth inhibitory profile of β-lapachone in combination with Taxol® against ovarian tumor cell lines as determined by MTT assay;

DETAILED DESCRIPTION OF THE INVENTION

Figure 1:
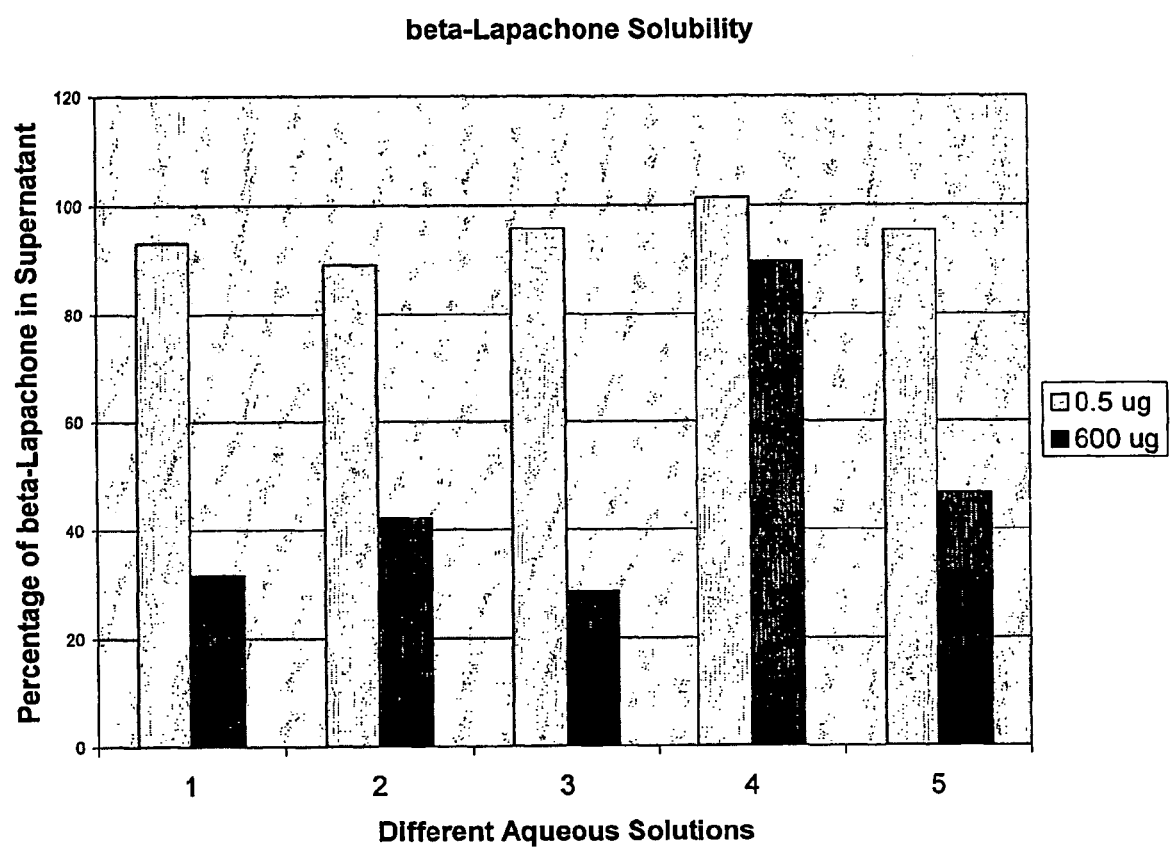
FIG. 1 is a bar graph illustrating the relative solubility of β-lapachone in aqueous solutions of various solubilizing agents.

β-lapachone, as well as its derivatives and analogs thereof (also referred to herein as the "active compounds"), are described in Li, C. J. et al., *J. Biol. Chem.,* 1993. These active compounds can be incorporated into pharmaceutical compositions suitable for parenteral administration. Such compositions typically comprise the active compound and a pharmaceutically acceptable carrier, excipient, diluent or adjuvant. However, the low solubility of β-lapachone in most pharmaceutically acceptable solvents has been an obstacle to the development of a suitable formulation for parenteral and topical administration, particularly intravenous and cutaneous administration, respectively. Table 1 illustrates the limited solubility of β-lapachone in common solvent systems used for intravenous delivery of drugs. Preclinical pharmacokinetic data produced to date suggest that the ideal peak plasma concentration is in the range of 10 μg/ml. To achieve this plasma concentration, an intravenous formulation must have a β-lapachone concentration approaching 10 mg/ml and be able to be diluted 5–×10× with sterile fluids for intravenous administration, such as saline or D5W.

TABLE 1

| Solvent System | β-lapachone Solubility (mg/ml) | |
| --- | --- | --- |
| | Undiluted (mg/ml) | 5X dilution* (mg/ml) |
| Poloxamer 20% | 2.0350 | 0.0331 |
| Povidone K17 20% | 1.8250 | 0.0312 |
| Povidone K12 20% | 1.8600 | 0.0313 |
| Tween 80 | 11.1700 | 1.6550 |
| EtOH 76% | 10.6600 | 0.1025 |
| PEG 400 | 11.6800 | 0.1400 |
| Propylene Glycol | 8.7800 | 0.0950 |
| Trappsol 20% | 1.4650 | 0.0300 |

*Diluted in 0.9% saline

The maximum solubility of β-lapachone in the solvents listed in Table 1 was about 12 mg/ml. Upon dilution, the solubility decreased more than the dilution factor in all the systems. Although various preclinical studies have used a variety of common solvent systems, such as lipiodol, peanut oil, Cremophor/ethanol or PEG4000, for i.p. and i.v. dosing, none of these approaches have yet demonstrated suitability for development of an i.v. formulation for use in the clinic. Combining, mixing and/or complexing β-lapachone, its derivatives or analogs, with a pharmaceutically-acceptable water-solubilizing carrier molecule, which is advantageously hydroxypropyl-β-cyclodextrin (HPBCD) increases the aqueous solubility of β-lapachone with concentrations as high as 20 mg/ml in 50% HPBCD solution as illustrated in Table 2.

TABLE 2

| HPBCD in Water | β-lapachone (highest conc.) (mg/ml) |
| --- | --- |
| 10% | 3.07 |
| 20% | 7.04 |
| 30% | 10.78 |
| 40% | 15.77 |
| 50% | 19.74 |

These β-lapachone/HPBCD solutions are stable for extended periods at room temperature and can be further diluted with sterile fluids for IV administration (e.g., sterile saline, D5W) and held for at least 24 hours without precipitation of β-lapachone. The β-lapachone/HPBCD solutions may also be sterile filtered, lyophilized and readily reconstituted in water. Experimentation has determined that HPBCD@20%/β-lapachone@5 mg/ml provides an excellent concentration for easy lyophilization and relatively fast reconstitution. The invention is not limited in this respect, however, and concentrations of β-lapachone as low as 1 mg/ml have been prepared and determined to be stable and capable of being lyophilized and reconstituted. The combining or complexation of β-lapachone with HPBCD also appears to improve the stability of β-lapachone to photoreduction compared with complexation of β-lapachone with ethanol solutions.

Further study of β-lapachone in aqueous HPBCD solutions has demonstrated that the solubility of β-lapachone increases linearly with the increase in HPBCD concentration. Upon 10 to 100 times dilution, the decrease of β-lapachone concentration in all HPCD systems is proportional to the dilutions made.

Cyclodextrins are crystalline, nonhygroscopic cyclic oligomers of α-D-glucopyranose derived from starch. As a result of a lack of rotation about the bonds connecting the glucopyranose units, the cyclodextrins are not cylindrical, but toroidal in shape. Because of this restricted rotation they have a rigid structure with a central cavity whose size varies according to the number of glucopyranose units in the molecule. The three most common cyclodextins are α-cyclodextrin, β-cyclodextrin and γ-cyclodextrin, and which consist of six, seven and eight glucopyranose units respectively. Due to the arrangement of hydroxyl groups within the cyclodextrin molecule and the shape of the molecule, the internal surface of the cavity is hydrophobic, while the outside surface is hydrophilic. The primary hydroxyl groups are located on the narrower (inner) side of the toroidal molecule, while the secondary hydroxyl groups are located on the wider (outer) edge. This arrangement permits the cyclodextrins to accommodate a wide variety of small hydrophobic molecules within the hydrophobic cavity by forming an inclusion complex.

The HPBCD has seven glucopyranose units and has hydroxypropyl groups attached to each glucopyranose unit on the outer surface of the toroidal structure. The solubility of HPBCD in water has been shown to be far superior than that of β-cyclodextrin. The introduction of the hydroxypropyl groups into the β-cyclodextrin renders it more soluble by disrupting the intramolecular hydrogen bonding between hydroxyl moieties on the cyclodextrin cavity. As a result, inclusion complexes formed by HPBCD will also have higher solubility in water compared to inclusion complexes formed by β-cyclodextrins. The degree of substitution determines the solubility and complexation patterns. The lesser the substitution, the more the binding will be similar to that of unsubstituted cyclodextrin in terms of binding, as well as solubility. Higher substitution renders the cyclodextrin more soluble in water but less binding. The degree of substitution of cyclodextrins is easily controlled.

When complexing β-lapachone, its derivatives or analogs, with a water-solubilizing carrier molecule in accordance with the present invention, the complexed solution generally becomes a unitary composition, or in the case where the water-solubilizing carrier molecule is a HPBCD, an inclusion complex is formed wherein the insoluble β-lapachone, its derivatives or analogs, is within the cyclodextrin cavity. The invention is not limited, however, to the formation of a complex.

Although HPBCD is the preferred solubilizing agent, the invention is not limited in this respect, and other water-solubilizing agents for combining with β-lapachone, its derivatives or analogs, such as Poloxamer, Povidone K17, Povidone K12, Tween 80, ethanol, Cremophor/ethanol, polyethylene glycol 400, propylene glycol and Trappsol, are contemplated. Furthermore, the invention is not limited to water-solubilizing agents, and oil-based solubilizing agents such as lipiodol and peanut oil, may also be used.

Surfactants are also contemplated as part of the present invention for solubilization of β-lapachone, its derivatives or analogs. It is necessary, however that the surfactant(s) used must be present at a high enough level when β-lapachone, its derivatives or analogs, is diluted in water so that there is sufficient surfactant to retain the β-lapachone, derivative or analog in solution. However, there cannot be too much surfactant to cause intolerable side effects.

Emulsions of β-lapachone, its derivatives or analogs, may also be formed and are contemplated by the present invention. Emulsions may be prepared which comprise a therapeutically effective amount of β-lapachone, its derivatives or analogs, in one or more emulsifiers or emulsifying agents which may result in an oil-in-water-type emulsion for parenteral administration. Suitable emulsifiers or emulsifying agents may include, but are not limited to, any pharmaceutically acceptable emulsifier, preferably phospholipids extracted from egg yolk or soy bean, synthetic phosphatidyl cholines or purified phosphatidyl cholines from vegetable origin. Hydrogenated derivatives can also be used, such as phosphatidyl choline hydrogenated (egg) and phosphatidyl choline hydrogenated (soya). Emulsifiers may also be nonionic surfactants such as poloxamers (for example Poloxamer 188 and 407), poloxamines, polyoxyethylene stearates, polyoxyethylene sorbitan fatty acid esters or sorbitan fatty acid esters. Ionic surfactants may also be used such as cholic acid and deoxycholic acid or surface active derivatives or salts thereof. The emulsifier can also be a mixture of one or more of the above ingredients. The emulsion may additionally contain other ingredients such as buffers, stabilizers and other lipids.

Intralipid® is a fat emulsion for injection. Fat emulsions may contain egg yolks, soybean oil, and safflower oil. Intralipid®, marketed in the U.S. as Liposyn II® and Liposyn III® (Abbot Laboratories, Abbott Park, Ill.), may be used as a source of calories and fatty acids to maintain or increase the weight of the patient to whom it is administered, or it may be used as a vehicle for poorly water-soluble lipophilic drugs that cannot be injected directly. Intralipid® and Liposyn II® are marketed in both a 10% and 20% concentration. In accordance with the present invention, an emulsion comprising β-lapachone, its derivatives or analogs, and Intralipid®, or any other pharmaceutically acceptable fat emulsion, may be prepared for parenteral administration to a patient.

Recent in vitro and in vivo studies have shown that β-lapachone demonstrates significant synergy with other chemotherapeutic and anticancer agents, particularly cis-platinum, and taxane derivatives, such as Taxol® (paclitaxel) (Bristol-Myers Squibb Co., New York, N.Y.). WO00/61142, for example, discloses a method and composition for the treatment of cancer, which comprises the administration of an effective amount of a first compound, a G1 or S phase drug, such as a β-lapachone, in combination with a G2/M drug, such as a taxane derivative. By virtue of both its major functional characteristics—synergy with other chemotherapy drugs and activity against resistant cells—the use of β-lapachone, its derivatives or analogs, may significantly increase the rate of long term remission of numerous cancers, including ovarian, breast, prostate, colon, pancreatic, multiple myeloma, malignant melanoma and non-melanoma skin cancers. β-lapachone, its derivatives or analogs may also be used to treat proliferation disorders and dermatologic conditions, such as psoriasis.

As recited, the pharmaceutical composition and formulations of the present invention are intended for parenteral administration, preferably intravenous administration. The invention is not, however, limited in this respect and liquid pharmaceutical compositions and formulations in accordance with the present invention may be prepared for oral ingestion.

Advantageously, pharmaceutical compositions for parenteral administration comprise a desired amount of β-lapachone, its derivatives or analogs, complexed with HPBCD. Regular β-cyclodextrins are not suitable for formulations intended for parenteral administration, but may be used for the preparation of formulations for oral administration. As recited, experimentation has determined that the solubility of β-lapachone, its derivatives or analogs, increases linearly with the increase in HPBCD concentration.

While β-lapachone is the preferred compound for use in the composition in accordance with the present invention, the invention is not limited in this respect, and β-lapachone derivatives or analogs, such as lapachol, and pharmaceutical compositions and formulations thereof are part of the present invention. Such β-lapachone analogs include those recited in PCT International Application PCT/US93/07878 (WO 94/04145), which is incorporated by reference herein in its entirety, and which discloses compounds of the formula:

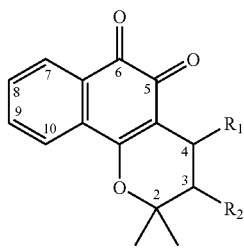

where R and $R_1$ are each independently hydrogen, substituted and unsubstituted aryl, substituted and unsubstituted alkenyl, substituted and unsubstituted alkyl and substituted or unsubstituted alkoxy. The alkyl groups preferably have from 1 to about 15 carbon atoms, more preferably from 1 to about 10 carbon atoms, still more preferably from 1 to about 6 carbon atoms. The term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to about 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms.

Other β-lapachone analogs contemplated in accordance with the present invention include those described in U.S. Pat. No. 6,245,807, which is incorporated by reference herein in its entirety, and which discloses β-lapachone analogs and derivatives having the stricture:

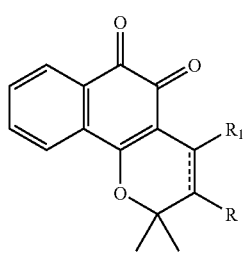

where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof, where the dotted double bond between the ring carbons represents an optional ring double bond.

Additional β-lapachone analogs and derivatives are recited in PCT International Application PCT/US00/10169 (WO00/61142), which is incorporated by reference herein in its entirety, and which disclose compounds of the structure:

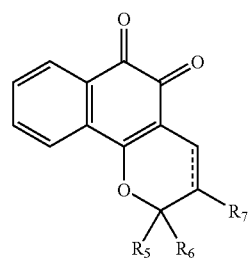

where $R_5$ and $R_6$ may be independently selected from hydroxy, $C_1$–$C_6$ alkyl, $C_1$–$C_6$ alkenyl, $C_1$–$C_6$ alkoxy, $C_1$–$C_6$ alkoxycarbonyl, —$(CH_2)_n$-phenyl; and $R_7$ is hydrogen, hydroxyl, $C_1$–$C_6$ alkyl, $C_1$–$C_6$ alkenyl, $C_1$–$C_6$ alkoxy, $C_1$–$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer from 0 to 10.

Other β-lapachone analogs and derivatives are disclosed in U.S. Pat. Nos. 5,763,625, 5,824,700 and 5,969,163, as well is in scientific journal articles, such as Sabba et al, *J Med Chem* 27:990–994 (1984), which discloses β-lapachone with substitutions at one or more of the following positions: 2-, 8- and/or 9-positions. See also Portela et al., *Biochem Pharm* 51:275–283 (1996) (substituents at the 2- and 9-positions); Maruyama et al, *Chem Lett* 847–850 (1977); Sun et al., *Tetrahedron Lett* 39:8221–8224 (1998); Goncalves et al, *Molecular and Biochemical Parasitology* 1:167–176 (1998) (substituents at the 2- and 3-positions); Gupta et al., *Indian Journal of Chemistry* 16B: 35–37 (1978); Gupta et al., *Curr Sci* 46:337 (1977) (substituents at the 3- and 4-positions); DiChenna et al., *J Med Chem* 44: 2486–2489 (2001) (monoarylamino derivatives). Each of the above-mentioned references are incorporated by reference herein in their entirety.

More preferably, analogs and derivatives contemplated by the present application are intended to encompass compounds having the general formula I and II:

Formula I

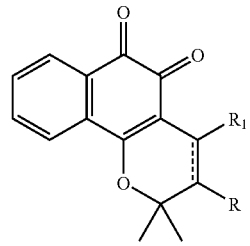

-continued

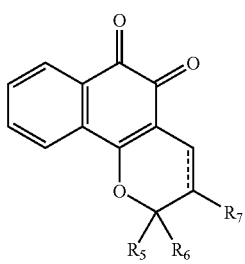

Formula II where the dotted double bond between the ring carbons represents an optional ring double bond and where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof. The alkyl groups preferably have from 1 to about 15 carbon atoms, more preferably from 1 to about 10 carbon atoms, still more preferably from 1 to about 6 carbon atoms. The term alkyl refers to both cyclic and noncyclic groups. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups having from 1 to 10 carbon atoms or from 1 to 6 carbon atoms, alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms; and where $R_5$ and $R_6$ may be independently selected from hydroxy, $C_1$–$C_6$ alkyl, $C_1$–$C_6$ alkenyl, $C_1$–$C_6$ alkoxy, $C_1$–$C_6$ alkoxycarbonyl, —$(CH_2)_n$-heteroaryl, —$(CH_2)_n$-heterocycle, or —$(CH_2)_n$-phenyl; and $R_7$ is hydrogen, hydroxyl, $C_1$–$C_6$ alkyl, $C_1$–$C_6$ alkenyl, $C_1$–$C_6$ alkoxy, $C_1$–$C_6$ alkoxycarbonyl, —$(CH_2)_n$-amino, -aryl, —$(CH_2)_n$-heteroaryl, —$(CH_2)_n$-heterocycle, or —$(CH_2)_n$-phenyl, wherein n is an integer from 0 to 10.

Preferred analogs and derivatives also contemplated by the invention include compounds of the following general formula III:

Formula III where $R_1$ is $(CH_2)_n$—$R_2$, where n is an integer from 0–10 and $R_2$ is hydrogen, an alkyl, an aryl, a heteroaromatic, a heterocyclic, an aliphatic, an alkoxy, an allyloxy, a hydroxyl, an amine, a thiol, an amide, or a halogen.

Analogs and derivatives also contemplated by the invention include 4-acetoxy-β-lapachone, 4-acetoxy-3-bromo-β-lapachone, 4-keto-β-lapachone, 7-hydroxy-β-lapachone, 7-methoxy-β-lapachone, 8-hydroxy-β-lapachone, 8-methoxy-β-lapachone, 8-chloro-β-lapachone, 9-chloro-β-lapachone, 8-methyl-β-lapachone and 8,9-dimethoxy-β-lapachone.

Preferred analogs and derivatives also contemplated by the invention include compounds of the following general formula IV:

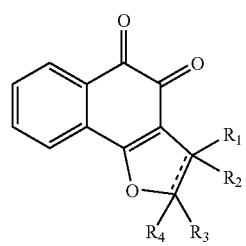

Formula IV where $R_1$–$R_4$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, or —$(CH_2)_n$-phenyl; or $R_1$ and $R_2$ combined are a single substituent selected from the above group, and $R_3$ and $R_4$ combined are a single substituent selected from the above groups, in which case —, — is a double bond.

Preferred analogs and derivatives also contemplated by this invention include dunnione and 2-ethyl-6-hydroxynaphtho[2,3-b]-furan-4,5-dione.

Preferred analogs and derivatives also contemplated by the invention include compounds of the following general formula V:

Formula V where $R_1$ is selected from H, $CH_3$, $OCH_3$ and $NO_2$.

Figure 12:
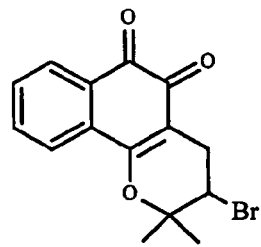
FIG. 12 illustrates preferred β-lapachone analogs and derivatives in accordance with the present invention.
Figure 12:
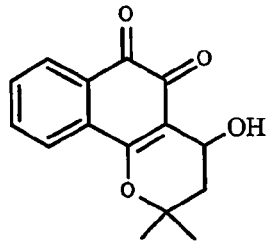
Figure 12:
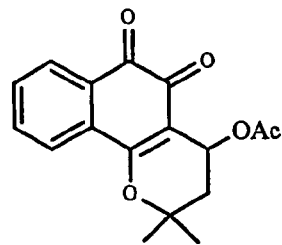
Figure 12:
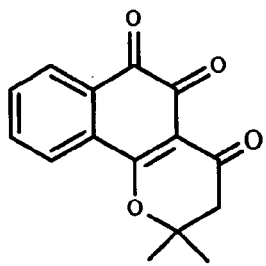
Figure 12:
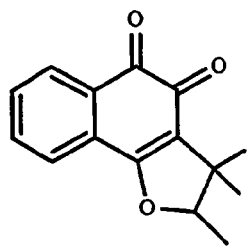
Figure 12:
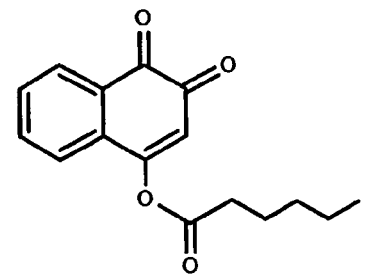
Figure 12:
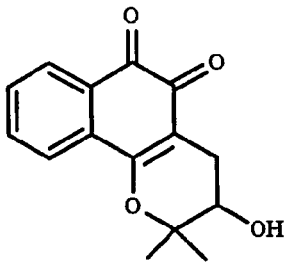
Figure 12:
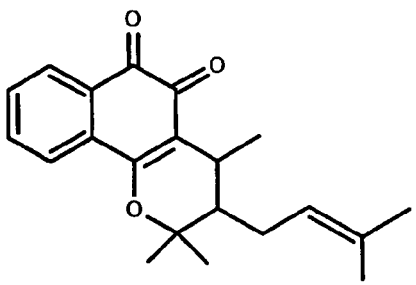
Figure 12:
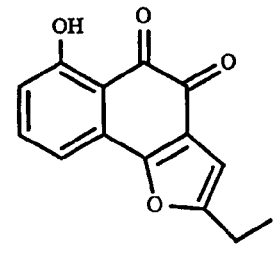

Preferred compounds of the above generic formulas are illustrated in FIG. 12.

The solubilities of β-lapachone and its analogs in 40% (w/v) HPBCD solution as compared to water are shown in Tables 3 and 4. To determine solubilities, test compounds were first dissolved in ethanol to prepare standard solutions with concentrations in the range 2.5–10 mg/ml, then were diluted with to 10 μg/ml with water. UV scans were obtained of the 10 μg/ml standard solutions, and the wavelength of maximum absorbance and the absorbance at the maximum absorbance wavelength were determined. For each test compound 50 μl aliquots of water and of 40% HPBCD were added to individual Eppendorf tubes containing approximately 1 mg of compound each. The tubes were heated in a 30° C. waterbath, vortexed, then centrifuged at 15,000 rpm for 5 min. This step was repeated, then the tubes were cooled to room temperature for 1 hour, then were centrifuged again. The supernatant from each tube was diluted with water into the appropriate absorbance range, and the UV absorbance was measured at the compound's absorbance maximum wavelength. The concentrations of these saturated solutions were then calculated by ratio to the 10 μg/ml ethanolic standard solutions. As shown in Tables 3 and 4 aqueous solubilities of the test compounds were increased by 7 to 323 fold in the presence of 40% HPBCD.

TABLE 3

Absorbance values of β-lapachone and its analogs in aqueous and in 40% (w/v) hydroxypropyl-β-cyclodextrin (HPBCD) solution

| Compound | Wavelength at Maximum Absorbance, (nm) | Absorbance of 10 μg/ml standard solution | Aqueous Solution Dil Factor | Aqueous Solution Absorbance | HPBCD Solution Dil Factor | HPBCD Solution Absorbance |
|---|---|---|---|---|---|---|
| β-Lapachone (βL) | 258 | 1.041 | 10 | 0.452 | 2000 | 0.73 |
| 3-Bromo-βL | 256 | 0.788 | 10 | 0.286 | 1000 | 0.545 |
| 3,4-dehydro-βL | 262 | 0.71 | 10 | 0.171 | 1000 | 0.41 |
| Dunnione | 262 | 0.944 | 100 | 0.449 | 5000 | 0.322 |
| 4-Acetoxy-βL | 254 | 0.89 | 50 | 0.506 | 500 | 0.373 |
| 4-Hydroxy-βL | 254 | 0.973 | 50 | 0.742 | 500 | 0.596 |
| 4-keto-βL | 280 | 1.216 | 50 | 1.224 | 500 | 1.07 |
| 3-Hydroxy-βL | 256 | 0.995 | 200 | 0.687 | 2000 | 0.727 |
| 3-(3-methyl-2-butenyl)-βL | 258 | 0.697 | 20 | 0.233 | 1000 | 0.284 |

TABLE 4

Solubilities of β-lapachone and its analogs in aqueous and in 40% (w/v) hydroxypropyl-β-cyclodextrin (HPBCD) solution

| Compound | Solubility in Water (μg/ml) | Solubility in HPBCD Solution (mg/ml) | Solubility Enhancement (–Fold) |
|---|---|---|---|
| β-Lapachone (βL) | 43 | 14.0 | 323 |
| 3-Bromo-βL | 36 | 6.9 | 191 |
| 3,4-dehydro-βL | 24 | 5.8 | 240 |
| Dunnione | 476 | 17.0 | 36 |
| 4-Acetoxy-βL | 284 | 2.1 | 7.4 |
| 4-Hydroxy-βL | 381 | 3.1 | 8.0 |
| 4-keto-βL | 503 | 4.4 | 8.7 |
| 3-Hydroxy-βL | 1381 | 14.6 | 10.6 |
| 3-(3-methyl-2-butenyl)-βL | 67 | 4.1 | 61 |

Other particular formulations in accordance with the present invention are set forth herein below and in the Examples section. In general, the β-lapachone, its derivative and analog, compounds may be prepared in a number of ways well known to one skilled in the art of organic synthesis. β-lapachone and its derivatives and analogs may be synthesized using methods generally described below, together with synthetic methods known in the art of synthetic organic chemistry, or variations thereon as appreciated by those skilled in the art. Preferred methods include, but are not limited to, those synthesis and formulation methods described herein.

Numerous methods are known in the art for synthesizing β-lapachone and/or derivatives or analogs thereof A first method is described in Schaffner-Sabba, K., et al., β-Lapachone: Synthesis of Derivatives and Activities in Tumor Models, *J. Med. Chem.*, 27, (1984) 990–994, and is known as the potassium salt method. A second method is described in Sun, J. S. et al., A Preparative Synthesis of Lapachol and Related Naphthoquinones, *Tetrahedron Letters*, 39 (1998) 8221–8224), and is know as the lithium salt method. These two methods both initially produce lapachol, an intermediate from which β-lapachone is synthesized. Both of these methods require the formation of a metal salt. Additionally, Amaral, A., et al., in The Total Synthesis of β-lapachone, *J. Heterocyclic Chem.*, 29 (1992) 1457–1460, describes the synthesis of β-lapachone α-naphthol in eight steps and results in an overall yield of only 23%. In U.S. Pat. No. 5,763,625, lapachol is first converted into 3-bromolapachone, which is then converted in a two-step sequence into 3-hydroxy-β-lapachone. Furthermore, as described in co-pending U.S. patent application Ser. No. 09/975,776, unlike the reported methods in which a metal (lithium or potassium) salt of 2-hydroxy-1,4-naphtoquinone was prepared in situ by addition of lithium hydride or separately by addition of potassium hydroxide to the quinone solution as the first step and then reacting the metal salt with bromide compound to form lapachol, the process described in co-pending U.S. patent application Ser. No. 09/975,776 eliminates this first step and commences directly with 2-hydroxy-1,4-naphthoquinone to react with 1-bromo-3-methyl-2-butene in the presence of sodium iodide and a weak base such as triethylamine, pyridine, trimethylamine, N,N-diisopropylethylamine, 2,6-lutidine, to form lapachol from which β-lapachone is subsequently synthesized.

As discussed above, β-lapachone as a single agent has been shown to have significant cytotoxic activity for a wide variety of cancel cell lines, with $IC_{50}$ values in the low (1–10) micromolar range. In vitro studies have demonstrated that these micromolar concentrations of β-lapachone totally abolished colony formation when applied to tumor cell cultures in combination with $IC_{50}$ levels of Taxol®. These studies have further shown that β-lapachone acts synergistically with Taxol®, which contains the active compound paclitaxel, to significantly augment effectiveness of either agent alone without attendant increases in toxicity (Li, C. J. et al., *Proc Natl Acad Sci U.S.A.* 96 (1999) 13369).

Potent inhibition of in vivo tumor growth by β-lapachone plus Taxol® has been demonstrated in a xenograft model of human ovarian cancer in nude mice. Potent antitumor activity has also been demonstrated in female nude mice bearing human breast cancer xenografts (discussed in detail in the Examples below).

Solubilized β-lapachone, its derivatives and analogs, may also be combined with other taxane derivatives and anticancer agents. In the combination, solubilized β-lapachone, its derivatives and analogs, may be admixed with the anticancer agent or taxane derivative, and provided in a single vial, or they may each be provided in a separate vial. When the solubilized β-lapachone, its derivatives and analogs, and the anticancer agent or taxane derivative is provided in separate vials, the contents of each vial may be administered to the patient simultaneously or sequentially.

In another embodiment, solubilized β-lapachone, its derivatives and analogs, may be administered in combination with radiation therapy. Advantageously, a patient will undergo radiation therapy a predetermined number of hours prior to or following β-lapachone, its derivatives and analogs, administration as determined by the medical clinician treating the patient.

The type and amount of β-lapachone, its derivatives and analogs, and the HPBCD or other carrier used will vary widely depending on the species of the warm blooded animal or human, body weight, and tumor being treated. Likewise, the dosage administered will vary depending upon known factors, such as the pharmacodynamic characteristics of the particular agent and its mode and route of administration, the age, health and weight of the recipient; the nature and extent of the symptoms; the kind of concurrent treatment; the frequency of treatment; and the effect desired.

The dosage administered will vary depending upon known factors such as the pharmacodynamic characteristics of the particular active ingredient, and its mode and route of administration; age, sex, health, metabolic rate, absorptive efficiency and/or weight of the recipient; nature and extent of symptoms; kind of concurrent treatment, frequency of treatment; and the effect desired. In a preferred embodiment, the dosage can be between approximately 0.1 mg/kg to 10 mg/kg administered from between twice weekly to once every four weeks.

As used herein, the term "therapeutically effective amount" means that amount of a drug or pharmaceutical agent that will elicit the biological or medical response of a tissue, system animal or human that is being sought by a researcher or clinician.

It is especially advantageous to formulate oral or parenteral compositions in dosage unit form for ease of administration and uniformity of dosage. A dosage unit may comprise a single compound, i.e., β-lapachone, its derivatives and analogs, or mixtures thereof with other compounds or other cancer inhibiting compounds or tumor growth inhibiting compounds or anti-viral compounds. Compositions suitable for parenteral administration advantageously include aqueous sterile injection solutions, but may also include non-aqueous solutions, which may contain antioxidants, buffers, bacteriostats and solutes which render the formulation isotonic with the blood of the intended recipient; and aqueous and non-aqueous sterile suspensions which may include suspending agents and thickening agents. The formulations may be present in unit-dose or multi-dose containers, for example, sealed in ampules and vials, and as discussed herein, may be stored in lyophilized condition requiring only the addition of the sterile liquid carrier, for example, water, for injections, immediately prior to use. Dosage unit form as used herein refers to physically discrete units suited as unitary dosages for the subject to be treated; each unit containing a predetermined quantity of active compound calculated to produce the desired therapeutic effect in association with the required pharmaceutical carrier. Extemporaneous injection solutions and suspensions may be prepared from sterile powders, granules and tablets as known in the art for the preparation of such solutions. The specifications for the dosage unit forms of the invention are dictated by and directly dependent on the unique characteristics of the active compound and the particular therapeutic effect to be achieved, and the limitations inherent in the art of compounding such an active compound for the treatment of individuals.

It should be understood that in addition to the ingredients particularly mentioned with regard to the specific compositions and formulations of the present invention, the compositions and formulations of this invention may include other agents convention in the art having regard to the type of formulation in question, for example, those suitable for oral administration may include flavoring and coloring agents.

In addition to the complex of β-lapachone, its derivatives and analogs, with HPBCD in accordance with the present invention, pharmaceutical compositions suitable for parenteral administration via injection or infusion may also include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), oil and suitable mixtures thereof. In all cases, the composition must be sterile and should be fluid to the extent that easy syringeability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin. Parenteral and intravenous compositions may also include minerals and other materials to facilitate their compatibility with the type of injection or delivery system to be used. Additionally, solutions for parenteral administration may contain a water soluble salt of the active compound, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The β-lapachone, derivative or analog complexes described herein can be freeze-dried, then reconstituted in aqueous solution and be substantially soluble (see Example 5 below).

For oral administration in liquid dosage form, the oral drug components are preferably combined with β-cyclodextrin and more preferably hydroxylpropyl-β-cyclodextrin, however the invention is not limited in this respect, and the oral drug components may be combined with any oral, non-toxic, pharmaceutically acceptable inert carriers such as ethanol, glycerol, water, oils and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Liquid dosage forms for oral administration can also contain coloring and flavoring to increase patient acceptance.

Additional examples of suitable liquid dosage forms may include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may also contain, additional solvents, preservatives, emulsifying agents, suspending agents, diluents, sweeteners, thickeners, and melting agents.

The active compounds may also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active compounds of this invention are intended for administration as treatment for cancer and the inhibition of tumors, by any means that produces contact of the active compounds with the agent's site of action in the body. As recited, the preferred mode of administering the β-lapachone, its derivatives and analogs, active ingredient is via parenteral administration, preferably intravenous administration (bolus or infusion). The invention is not however limited in this respect, and the active ingredients in accordance with this invention can be administered by any conventional means available for use in conjunction with pharmaceuticals, either as individual therapeutic agents or in a combination with other therapeutic agents with the intention of inhibiting tumors. For example, the active compounds may also be administered intraperitoneally, subcutaneously, or intramuscularly. The active compounds may also be formulated for topical administration for the treatment of skin cancers such as basal-cell carcinoma, squamous-cell cancer, Kaposi's sarcoma and melanoma. The active compounds can be administered alone, but generally are administered with a pharmaceutical carrier selected on the basis of the chosen route of administration and standard pharmaceutical practice.

The present invention also includes methods for treating cancer by administering to a patient the compositions and formulations of the present invention. In a preferred embodiment, the method comprises the parenteral administration of the compositions and formulations to a patient, preferably via intravenous injection or infusion as described above. In another embodiment, the method comprises the topical administration of the compositions and formulation of the invention. "Topical application", "applied topically", "topical administration" and "administered topically", are used interchangeably to mean the process of applying or spreading one or more compositions according to the instant invention onto the surface of the skin of a subject in need thereof. Topical formulations may be comprised of an oil-in-water cream emulsion but is not limited in this respect. Topical formulations contemplated by the present invention may include delayed release compositions capable of producing a slow release of the β-lapachone analogs and derivatives.

The formulations for topical administration may optionally contain a wide variety of additional components intended to improve the overall desirability, visual appearance, physical properties and/or physical feel, but provided that such optional additives are physically and chemically compatible with the essential components described herein (supra), and do not unduly impair stability, safety or efficacy. Optional additives may be dispersed, dissolved or the like in the carrier of the present compositions. Optional additives include possible aesthetic agents, (e.g., absorbents including oil absorbents in the form of cosmetic clays and polymeric absorbents), abrasives, anti-caking agents, antifoaming agents, additional anti-microbial agents, binders, buffering agents, bulking agents, cosmetic biocides, additional denaturants and penetrants (supra), cosmetic astringents, drug astringents, external analgesics, film formers, opacifying agents, fragrances, perfumes, pigments, colorings, skin soothing agents, pH adjusters, chelating agents, UV light absorbing agents, plasticizers, preservatives, preservative enhancers, depiliating agents, desquamation agents and exfoliants, collagens and breakdown products thereof, film-forming agents and the like. Representative examples of such materials are disclosed in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962–1965); and in The Handbook of Cosmetic Science and Technology, 1st Ed. Knowlton & Pearce (Elsevier 1993).

In other embodiments, compositions for use according to the methods of the invention also include compositions having a hydrophilic and hydrophobic phase. Non-limiting examples of suitable non-natural hydrophobic phase components include: (i) a non-toxic and non-carcinogenic mixtures of liquid hydrocarbons obtained from petroleum (64, 65); (ii) a non-toxic, non-carcinogenic colloidal system of nonstraight-chain solid hydrocarbons and high-boiling liquid hydrocarbons in which most of the liquid hydrocarbons are micellar (64, 66, 67); (iii) non-toxic and noncarcinogenic straight and branched chain hydrocarbons having from about 7 to about 40 carbon atoms, e.g., dodecane, isododecane, squalane, cholesterol, hydrogenated polyisobutylene, docosane (i.e. a $C_{22}$ hydrocarbon), hexadecane, isohexadecane (Permethyl.RTM 101A, Presperse, South Plainfield, N.J.), and the like; (iv) non-toxic and non-carcinogenic $C_{1-30}$ alcohol esters of $C_{1-30}$ carboxylic acids and of $C_{2-30}$ dicarboxylic acids, including straight and branched chain materials as well as aromatic derivatives (e.g., diisopropyl sebacate, diisopropyl adipate, isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, distearyl stearate, isopropyl stearate, methyl stearate, cetyl stearate, behenyl behenrate, dioctyl maleate, dioctyl sebacate, diisopropyl adipate, cetyl octanoate, diisopropyl dilinoleate. (v) non-toxic and non-carcinogenic mono-, di- and triglycerides of $C_{1-30}$ carboxylic acids, e.g., caprilic/capric triglyceride, PEG-6 caprylic/capric triglyceride, PEG-8 caprylic/capric triglyceride. (vi) non-toxic and non-carcinogenic alkylene glycol esters of $C_{1-30}$ carboxylic acids, e.g., ethylene glycol mono- and di-esters, and propylene glycol mono- and di-esters of $C_{1-30}$ carboxylic acids e.g., ethylene glycol distearate; (vii) non-toxic and non-carcinogenic propoxylated and ethoxylated derivatives of the foregoing materials; and (viii) non-toxic and non-carcinogenic $C_{1-30}$ mono- and poly-esters of monosaccharides and oligosaccharides. Examples of liquid esters that may prove useful in the hydrophobic phase include glucose tetra-oleate; glucose tetra-esters of soybean oil fatty acids (unsaturated); mannose tetra-esters of mixed soybean oil fatty acids; galactose tetra-esters of oleic acid; arabinose tetra-esters of linoleic acid; xylose tetra-linoleate; galactose penta-oleate; sorbitol tetra-oleate; sorbitol hexa-esters of unsaturated soybean oil fatty acids; xylitol penta-oleate; sucrose tetra-oleate; sucrose pentaoletate; sucrose hexa-oleate; sucrose hepta-oleate; sucrose octa-oleate; and mixtures thereof.

In other embodiments, compositions suitable for topical administration according to the present invention include compositions having alternative carriers. Examples of alternative carriers include cross-linked polymeric compounds containing one or more monomers derived from acrylic acid, substituted acrylic acids, and salts and esters of these acrylic acids and the substituted acrylic acids, wherein the cross-linking agent contains two or more carbon-carbon double bonds and is derived from either (i) an acrylic acid homopolymeric polyhydric alcohol, e.g., crosslinked homopolymers of acrylic acid monomer or derivative thereof (e.g., $C_{1-4}$ alkyl, —CN, or —COOH substituted), where the acrylic acid has substituents at the two and three carbon positions (e.g., acrylic acid, methacrylic acid, ethacrylic acid, and mixtures thereof); or (ii) a cross-linked acrylate copolymer having both an acrylic acid monomer (or derivative thereof) and a $C_{1-4}$ alcohol acrylate ester monomer (or derivative thereof), and a second monomer which is a long chain alcohol (e.g. $C_{8-40}$) acrylate ester monomer (or derivative thereof), e.g., acrylic acid, methacrylic acid, ethacrylic acid, and mixtures thereof. Combinations of the latter two types of polymers are may also prove useful in certain compositions for use according to the treatment methods of the invention.

In addition to treating disorders such as skin cancers, the preparations of this invention may be used to treat a wide variety of dermatologic conditions or disorders. Dermatologic conditions can be any disorder associated with the skin. Dermatologic conditions include, but are not limited to, dermatitis conditions such as: Contact Dermatitis; Atopic Dermatitis; Seborrheic Dermatitis; Nummular Dermatitis; Chronic Dermatitis of Hands and Feet; Generalized Exfoliative Dermatitis; Stasis Dermatitis; and Localized Scratch Dermatitis; bacterial infections of the skin, such as: Staphylococcal Diseases of the Skin, Staphylococcal Scalded Skin Syndrome; Erysipelas; Folliculitis; Furuncles; Carbuncles; Hidradenitis Suppurativa; Paronychial Infections and Erythrasma; superficial fungal infections such as: Dermatophyte Infections; Yeast Infections; Candidiasis; and Tinea Versicolor; parasitic infections of the skin such as: Scabies; Pediculosis; and Creeping Eruption; disorders of hair follicles and sebaceous; glands such as: Acne; Rosacea; Perioral Dermatitis; Hypertrichosis; Alopecia; Pseudofolliculitis Barbae; and Keratinous Cyst; scaling papular diseases, such as: Psoriasis; Pityriasis Rosea; and Lichen Planus; pressure sores; benign tumors and malignant tumors.

Additional information with regard to the methods of making the compositions and formulations and the ingredients comprising the compositions and formulations in accordance with the present invention can be found in standard references in the field, such as for example, "Remington's Pharmaceutical Sciences", Mack Publishing Co., Easter, Pa., $15^{th}$ Ed. (1975).

The present invention also includes pharmaceutical kits which comprise one or more containers containing a pharmaceutical composition comprising a therapeutically effective amount of an active compound. Such kits may further include, if desired, one or more of various conventional pharmaceutical kit components, such as, for example, containers with one or more pharmaceutically acceptable carriers, additional containers, etc., as will be readily apparent to those skilled in the art. In a preferred embodiment, a kit is provided for the treatment of a mammalian cancer comprising at least one vial containing β-lapachone, or a derivative or analog thereof. In another preferred embodiment, a kit is provided for the treatment of a mammalian tumor comprising one or more vials containing a complex of a therapeutically effective amount of β-lapachone, or a derivative or analog thereof, and a pharmaceutically acceptable, water-solubilizing carrier molecule and further comprising, within in the same vial or a separate vial, an anticancer agent, particularly a taxane derivative.

Printed instructions, either as inserts or as labels, indicating quantities of the components to be administered, guidelines for administration, and/or guidelines for mixing the components, may also be included in the kit. In the present disclosure it should be understood that the specified materials and conditions are important in practicing the invention but that unspecified materials and conditions are not excluded so long as they do not prevent the benefits of the invention from being realized.

The invention is further defined by reference to the following examples, which are not meant to limit the scope of the present invention. It will be apparent to those skilled in the art that many modifications, both to the materials and methods, may be practiced without departing from the purpose and interest of the invention.

EXAMPLES

1. Evaluation of Acceptable Solvent Systems Known to Solubilize Hydrophobic Drug Substances a. Preparation of β-Lapachone and Hydroxypropyl-β-Cyclodextrin (HPBCD) Solution Various pharmaceutically acceptable solvent systems known to solubilize hydrophobic drug substances were evaluated with β-lapachone. As shown in Table 5 below, solutions meeting the targeted minimum concentration (10 mg/ml) were achieved in several of the solutions evaluated. However, none of these systems could be diluted 5× with sterile saline without significant precipitation of the β-lapachone from solution. In addition, most of these co-solvents and surfactants have their own toxicity and tolerability issues that need to be managed during high dose drug administration.

TABLE 5

| Solvent System | Undiluted (mg/ml) | 5X dilution* (mg/ml) |
| --- | --- | --- |
| Poloxamer (20%) | 2.0350 | 0.0331 |
| Povidone K17 (20%) | 1.8250 | 0.0312 |
| Povidone K12 (20%) | 1.8600 | 0.0313 |
| Tween 80 | 11.1700 | 1.6550 |
| EtOH (76%) | 10.6600 | 0.1025 |
| PEG 400 | 11.6800 | 0.1400 |
| Propylene Glycol | 8.7800 | 0.0950 |
| Trappsol (20%) | 1.4650 | 0.0300 |

*diluted in 0.9% saline

In light of the above, two different strategies were used to enhance β-lapachone solubility in aqueous solution. First, β-lapachone was treated with metal chelating agents, such as calcium and magnesium, to form soluble complexes; second, β-lapachone was treated with the solubilizing agents β-cyclodextrin and γ-cyclodextrin to form soluble inclusion complexes. In order to evaluate these four reagents, $^{14}$C-labeled β-lapachone in a small volume of ethanol was added to aqueous solutions of the reagents (or to PBS buffer as a control), then the relative solubility of β-lapachone in each of the solutions was measured in terms of radioactivity remaining in the supernatant after centrifugation.

Specifically, to individual 1.5 ml Eppendorf tubes containing 900 μl of PBS buffer were added the following: 8 mM CaCl$_2$ in PBS buffer, 8 mM of MgCl$_2$ in PBS buffer, 8 mM β-cyclodextrin in PBS buffer, and 8 mM γ-cyclodextrin in PBS buffer. 10 μl of C$^{14}$ labeled β-lapachone (40,000 CPM, 0.55 μg) in 75% ethanol was then added to each tube. After vortexing and centrifuging at 13,000 rpm for 10 min, 100 μl of the supernatant solution was counted for radioactivity using a Beckman Scintillation Counter. To the remaining mixture, 0.5 μg (50 μl of 10 mg/ml solution) or 600 μg of β-lapachone in 75% ethanol was added. After vortexing and centrifuging at 13,000 rpm for 10 min, 100 μl of the supernatant solution was counted again for radioactivity.

When 0.5 μg of β-lapachone was added, almost 100% of the β-lapachone was present in the supernatant for all five aqueous solutions. However, when 600 μg of β-lapachone was added, only β-cyclodextrin solution retained more than 50% of the β-lapachone in the supernatant. The percentage of labeled β-lapachone in the supernatant was determined by counting in a scintillation counter. FIG. 1 illustrates the relative solubility of β-lapachone in aqueous solutions of various solubilizing agents. In FIG. 1, solution 1 consisted of PBS buffer, solution 2 consisted of 8 mM CaCl$_2$ in PBS buffer, solution 3 consisted of 8 mM MgCl$_2$ in PBS buffer, solution 4 consisted of 8 mM β-cyclodextrin in PBS buffer, and solution 5 consisted of 8 mM γ-cyclodextrin in PBS buffer.

b. Effect of Hydroxypropyl-β-Cyclodextrin (HPBCD) Concentration on β-lapachone Solubility Because β-cyclodextrin is suitable for oral, but not for parenteral or topical use, its analog HPBCD was selected for further study. To examine the effect of HPBCD concentration on β-lapachone solubility, β-lapachone in small volumes of ethanol was added to eight aqueous solutions with varying concentrations of HPBCD (0–16 mM or 0–25% (w/w)), then relative solubility was determined by measuring the percentage of radioactivity remaining in the supernatant after centrifugation. In order to eliminate the possible effect of ethanol and determine if solubility enhancement can be maintained after lyophilization, the mixtures were lyophilized and then re-dissolved into the same volume of water. The percentage of β-lapachone in the supernatant of the re-dissolved mixture was measured to ensure complete resolubilization of the lyophilized material.

Specifically, to individual 1.5 ml Eppendorf tubes, sufficient amounts of water, 50 mM HPCD solution $^{14}$C-labeled β-lapachone solution in 75% ethanol, 10 mg/ml β-lapachone solution in ethanol, and 0.9% NaCl solution were added to prepare 1 ml solutions with component concentrations listed in the Table 6.

TABLE 6

| Tube # | 1 | 2 | 3 | 4 | 5 | 6 | 7 | 8 | 9 |
| --- | --- | --- | --- | --- | --- | --- | --- | --- | --- |
| HPCD, Mm | 0 | 0 | 1 | 2 | 4 | 6 | 8 | 12 | 16 |
| $^{14}$C-β-lapachone, CPM | 60K | 60K | 60K | 60K | 60K | 60K | 60K | 60K | 60K |
| β-lapachone, mM | 0 | 1 | 1 | 1 | 1 | 1 | 1 | 1 | 1 |
| NaCl, % (w/v) | 0.9 | 0.9 | 0.9 | 0.9 | 0.9 | 0.9 | 0.9 | 0.9 | 0.9 |

After vortexing and centrifuging at 13,000 rpm for 10 min, 100 μl of supernatant from teach tube was counted for radioactivity using a Beckman Scintillation Counter. The rest of the mixtures (900 μl each) were lyophilized and then re-dissolved in 900 μl of water. After vortexing and centrifuging at 13,000 rpm for 10 min, 100 μg/ml of supernatant from each tube was counted again for radioactivity.

Figure 2:
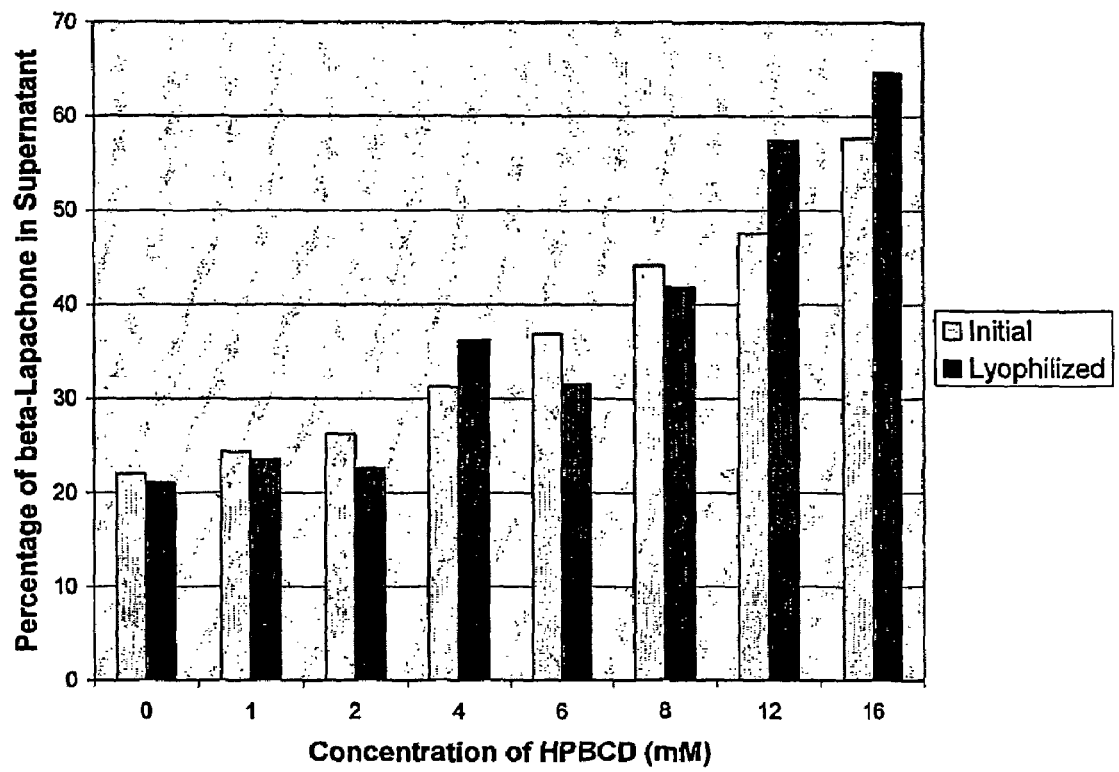
FIG. 2 is a bar graph illustrating the solubility of β-lapachone as a function of hydroxypropyl-β-cyclodextrin concentration (HPBCD)

FIG. 2 shows that β-lapachone solubility increases with increased HPBCD concentration, and that the β-lapachone can be fully resolubilized following lyophilization.

c. Preparation of β-lapachone and Hydroxypropyl-β-Cyclodextrin (HPBCD) Solution by Heating A β-lapachone/HPBCD solution was prepared without prior solubilization of the β-lapachone in ethanol solution. β-lapachone was combined with aqueous solutions of HPBCD in varying concentrations and the mixtures were heated to 70° C., then allowed to cool to room temperature. The cooled solutions were filtered (0.22μ), and the amount of the solubilized β-lapachone was measured by HPLC analysis. The solubility of β-lapachone in various aqueous solutions of HPBCD is provided in Table 7.

TABLE 7

| HPBCD % (m/M) | β-lapachone Conc. (mg/ml) |
| --- | --- |
| 50 (325) | 19.7 |
| 40 (260) | 15.8 |
| 30 (195) | 10.8 |
| 20 (130) | 7.4 |
| 10 (65) | 3.1 |

A maximum concentration of 19.7 mg/ml of β-lapachone was achieved in 50% HPBCD solution (highest concentration tested). The addition of saline or ethanol did not significantly enhance the solubility of β-lapachone in HPBCD.

d. HPLC Analysis and UV Measurement of β-lapachone Solution in 75% Ethanol and Aqueous Solution of β-lapachone-HPBCD Complex 5 μg/ml solutions of β-lapachone were prepared for HPLC and UV analysis by diluting either 200 μg/ml ethanolic solutions or 5 mg/ml HPBCD solutions with water. UV measurements at 258 nm were performed using routine procedures with 2% ethanol or 200 μg/ml HPBCD as reference solutions. For HPLC analysis, 100 μl of the resulting 5 μg/ml β-lapachone solutions was injected into a $C^{18}$ reverse phase analytical column, and a linear gradient from 25% to 75% B buffer in 10 min at flow rate of 1 ml/min was applied. Peaks were detected by UV absorption at 258 nm and quantitated by peak area ratio to external standards.

The $\lambda_{max}$ for β-lapachone was observed at 258 nm from the UV spectrum. UV measurements of β-lapachone solution at 258 nm showed an extinction coefficient of 26620 $M^{-1}$ $cm^{-1}$ for both β-lapachone alone and the β-lapachone-HPBCD complex.

Figure 3:
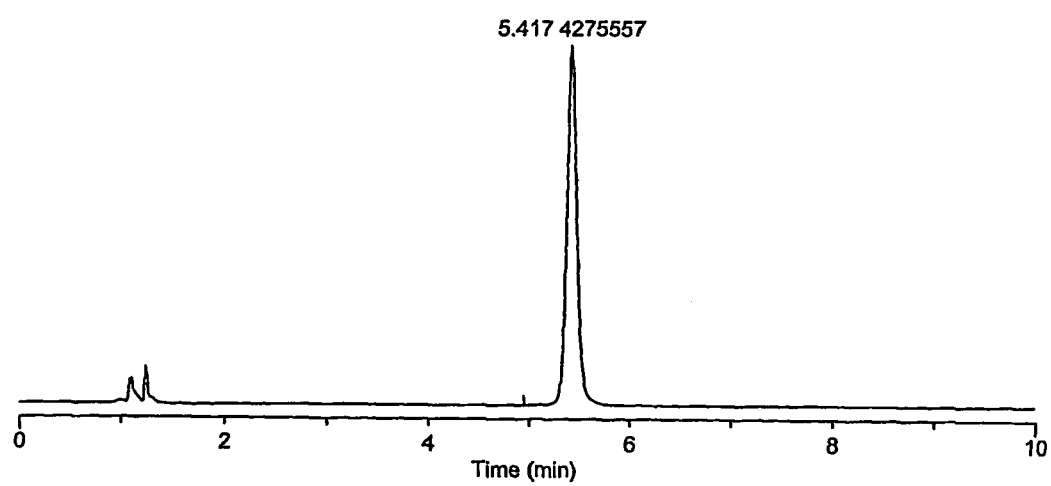
FIG. 3 is an HPLC chromatogram of a 5 mg/ml β-lapachone solution in 20% hydroxypropyl-β-cyclodextrin concentration.

FIG. 3 shows a typical HPLC chromatogram of a 5 mg/ml β-lapachone solution in 20% HPBCD, diluted to 5 μg/ml in water for HPLC analysis. β-lapachone elutes at approximately 5.4 min. Chromatograms showed no difference in retention times and peak integration areas between β-lapachone alone at 5 μg/ml in water and the comparable 5 μl/ml β-lapachone-HPBCD complex. These results suggest that the β-lapachone is not complexed with HPBCD at low concentrations (i.e., 5 μg/ml). When increasing quantities of HPBCD were added to the 5 μg/ml β-lapachone-HPBCD solution, HPLC analysis showed that a peak eluting at the void volume of the column (retention time of about 1.2 min) and presumed to be the β-lapachone-HPBCD complex, increased with size with a corresponding reduction of the β-lapachone peak. However, under the analytical conditions developed for β-lapachone quantitation, which requires dilution to 5 μg/ml, the integration of the peak at ~5.4 min provides accurate quantitation of the total β-lapachone in the solution.

e. β-lapachone Stability

The stability of β-lapachone solutions either in 75% ethanol or an aqueous β-lapachone-HPBCD complex form was monitored by HPLC analysis. When stored in the dark at room temperatures, the β-lapachone-HPBCD solution showed significantly better stability than the ethanolic solution. The HPBCD solution had no detectable degradation product peaks after 5 days of storage; and a single degradation product peak at about 0.1% at a retention time of 3.28 min after 21 days of storage. By comparison, ethanolic solutions stored in the dark showed significant loss of the β-lapachone peak after 5 days of storage. Significant stability enhancement was also observed for the β-lapachone-HPBCD solution as compared to β-lapachone in 75% ethanol solution when both were exposed to light with normal room brightness at room temperature. However, the β-lapachone-HPBCD solution is still appreciably degraded upon exposure to light, with degradation products comprising 3.4% of total peak area by day 21 of exposure.

The mechanism of degradation of β-lapachone in alcohol solutions has been shown to involve photoreduction to a relatively stable, semireduced quinone radical (Ci, Xiohong, et al., J. Am. Chem. Soc. 1989: 111, 1337–1343). In the above studies, the primary degradation product in ethanolic solutions was identified as the reduced (hydroquinone) form of β-lapachone through retention time comparisons with the product prepared by reduction of β-lapachone with sodium borohydride. This species, which elutes at approximately 6.9 min has not been detected in HPBCD solutions of β-lapachone, which seem to show a different degradative pathway.

2. Lyophilization of the β-lapachone/HPBCD Complex Solution

β-lapachone/HPBCD complex solution samples were prepared in accordance with the procedure set forth in Example 1a and 1c. The samples were transferred into a lyophilization container and pre-cooled to 40° C. for 2 h. Vacuum was applied to the container for 12–20 hours depending on the sample(s) (number, size, composition and other properties and characteristics of the samples) to provide a freeze-dried product.

The lyophilized sample(s) were reconstituted with 5.9 ml of deionized water with agitation to provide β-lapachone at 10 mg/ml. The results of the samples tested are shown in Table 8.

TABLE 8

β-lapachone/HPBCD system tested (All at 80 mg/vial)

| Formulation | Volume (ml) | Time to Dry/Reconstitute |
| --- | --- | --- |
| HPBCD @ 40%/β-lapachone @ 10 mg/ml (density = 1.125) | 8 | Long (~20 hr)/Long (>10 min) |
| HPBCD @ 26%/β-lapachone @ 6.7 mg/ml | 12 | Short (~13 hr)/Short (~10 min) |
| HPBCD @ 20%/β-lapachone @ 5 mg/ml | 16 | Short (~13 hr)/Short (~5 min) |
| HPBCD @ 10%/β-lapachone @ 2.5 mg/ml | 32 | Long (>20 hr) |

Based upon these results, HPBCD@40%/β-lapachone@10 mg/ml accomplished the solubility requirement for 10 to 100 times dilution. If the solution is stable under the storage conditions, it is a suitable parenteral solution without lyophilization. If lyophilization is preferred, HPBCD@20%/β-lapachone@5 mg/ml was demonstrated to be a good choice for speedy freeze-drying and relatively fast reconstitution.

3. In Vitro Study of β-lapachone Combined with Taxol®

Micromolar concentrations of β-lapachone have been shown to totally abolish colony formation when applied to tumor cell cultures in combination with $IC_{50}$ levels of Taxol®. In these studies, exponentially growing cells were seeded at 1,000 cells per well in six-well plates and allowed to attach for 48 h. β-lapachone and/or Taxol®, solubilized in DMSO, were added to the wells. Control wells were treated with equivalent volumes of DMSO. After 4 h cells were rinsed and fresh medium was added. Cultures were observed daily for 10–20 days and then were fixed and stained. Colonies of greater than 30 cells were scored as survivors. As shown in FIG. 4, synergistic inhibition of cancer cell survival was seen for a wide spectrum of human carcinoma cells of different histotypes, including ovarian, breast, prostate, melanoma, lung and pancreatic cell lines. β-lapachone or Taxol® alone were much less effective in decreasing cancer cell colony formation. The decreased cell survival was shown to be due to death by the MTT and tryptan blue exclusion assays. DNA laddering formation and annexin staining indicated that cell death was due to apoptosis.

Figure 6:
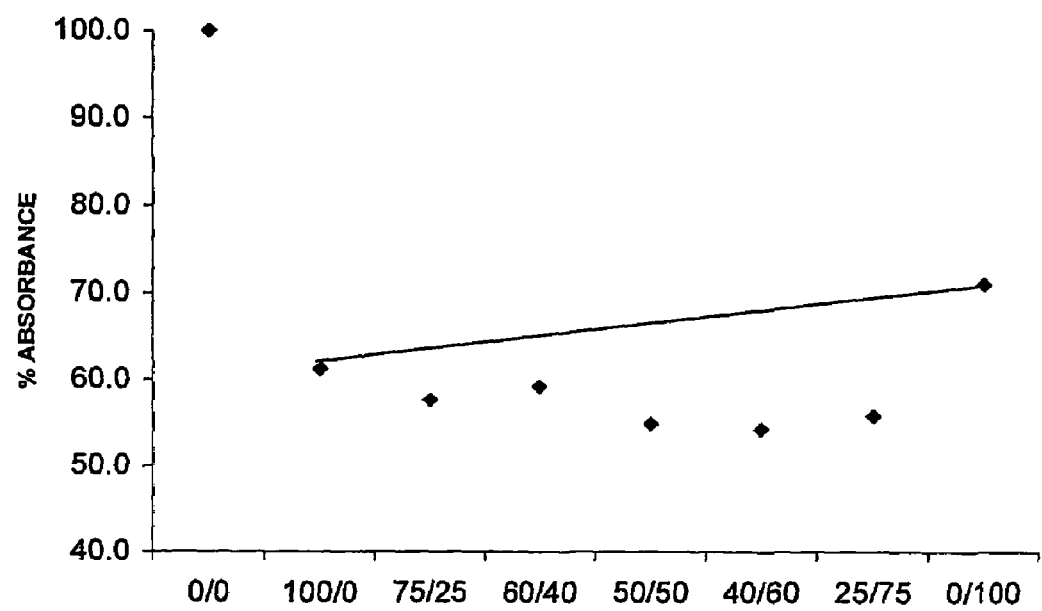
FIG. 6 is an isobologram showing synergistic drug-drug interaction for β-lapachone and Taxol® in the OVCAR-3 ovarian tumor cell line.
Figure 7:
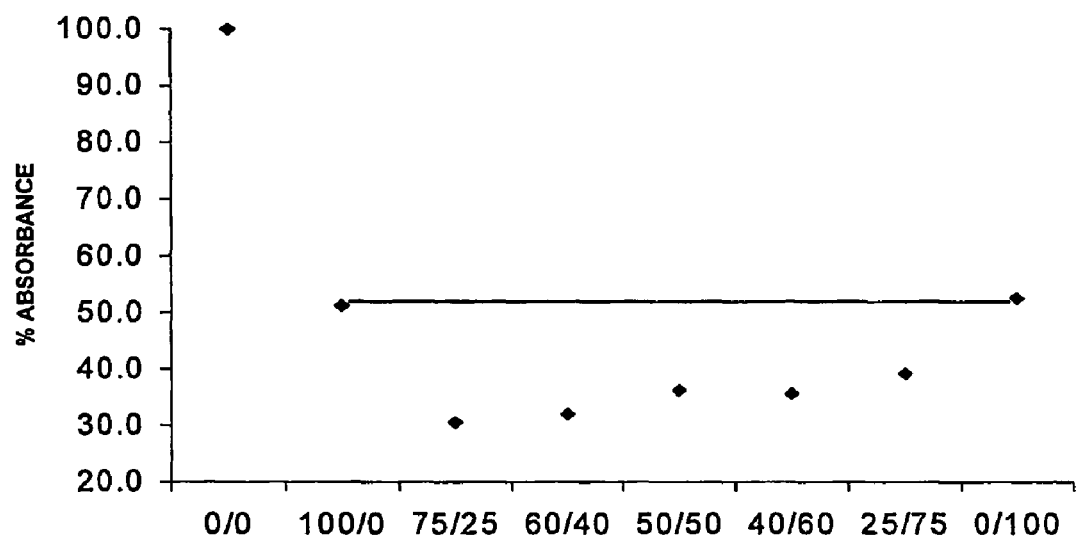
FIG. 7 is an isobologram showing synergistic drug-drug interaction for β-lapachone and Taxol® in the MDAH-2774 ovarian tumor cell line.

Drug-drug interaction of β-lapachone and Taxol® was further evaluated in two ovarian tumor cell lines, OVCAR-3 and MDAH-2774 using isobologram analysis. The individual $IC_{50}$ values for each drug were determined and then combinations of the two drugs at fixed ratios of their $IC_{50}$ concentrations were applied to the cells. Following a 4-day continuous exposure, cell viability was determined by MTT assay. As illustrated in FIGS. 5, 6 and 7, a pattern of synergistic cell kill was demonstrated by the combination of these two drugs in these cell lines.

Figure 8:
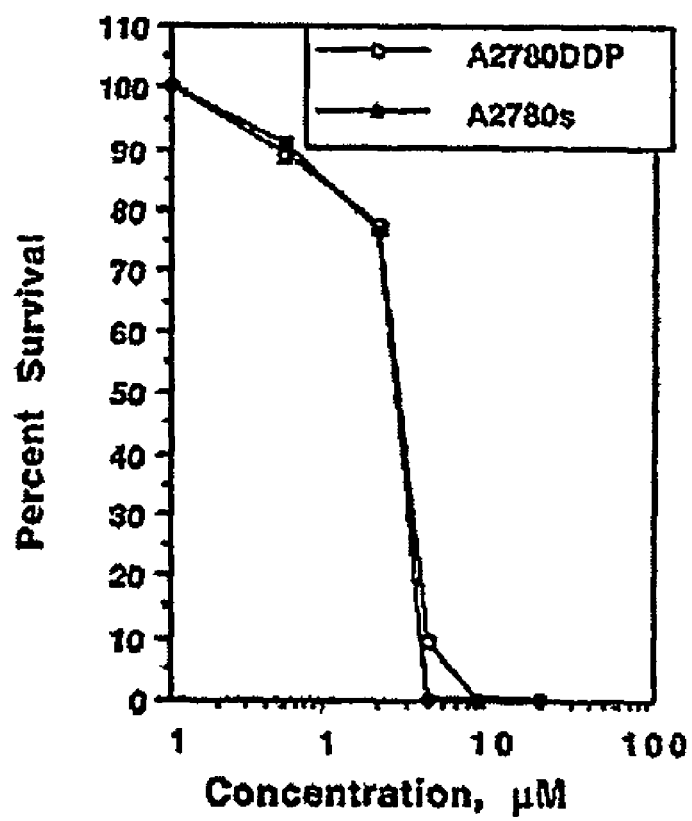
FIG. 8 is a graph illustrating the cytotoxic effect of β-lapachone on Cisplatin-sensitive (A2780s) and Cisplatin-resistant (A2780DDP) ovarian cancer lines.

In FIG. 5, when interpreting the combination curves, statistical comparisons were made with each test combination and the endpoints (100% β-lapachone and 100% Taxol®). A statistically significant observation requires that a difference exists between the combination (β-lapachone and Taxol®) absorbance value and both endpoint values (β-lapachone or Taxol® alone). If the majority of the values ($\geq 3$ of 5) are statistically ($p<0.05$) below the line, then synergy is described. In FIG. 6, the drug combination is shown to be significantly different ($p<0.05$) than either drug alone at 3 of the 5 combinations evaluated. In FIG. 7, the drug combination is shown to be significantly more cytotoxic ($p<0.05$) than either drug alone at 5 of the 5 combinations evaluated.

β-lapachone has also been shown to be active against cis-platinum-resistant cell lines. The ovarian line A2780DDP is highly cis-platinum (cisplatin) resistant, with an $IC_{50}$ concentration for cisplatin typically >100 µM. As shown in FIG. 8, β-lapachone as a single agent is equally cytotoxic to both the highly resistant line and to the parent line from which it is derived (A2780s). In testing β-lapachone against the cisplatin-resistant-cell lines, cells were exposed to β-lapachone solutions for 4 h. The cells were then rinsed and fresh medium was added. Cultures were observed daily for 10–20 days and then were fixed and stained. Colonies of greater than 30 cells were scored as survivors.

4. In Vivo Studies of β-lapachone Combined with Taxol®

Human ovarian cancer cells (36M2, originally isolated from malignant ascites) were inoculated by i.p. injection into athymic female nude mice 24 h after irradiation. In this model, metastatic foci form approximately 1 week after inoculation, and tumor nodules of the peritoneum and malignant ascites develop in 4–5 weeks. Ten days after tumor inoculation ($10 \times 10^6$ cells), treatment regimens were initiated. The control group was treated with vehicle alone. In each typical treatment cycle, the β-lapachone alone group was treated with 25–50 mg/kg i.p. of β-lapachone in Lipiodol solution and the Taxol® alone group was treated at 1 mg/kg i.p. (Taxol® formulation diluted in Lipiodol), both followed 24 h later by i.p. injection of vehicle. In the combination group, nude mice were treated with β-lapachone at 25–50 mg/kg, followed 24 h later by Taxol® at 1 mg/kg. All groups were treated for 10 cycles, with a 1-day break between each cycle. Mice were sacrificed two weeks later after the last treatment cycle (on day 50) to assess antitumor activity. Host toxicity was evaluated by general appearance and body weight.

Figure 9:
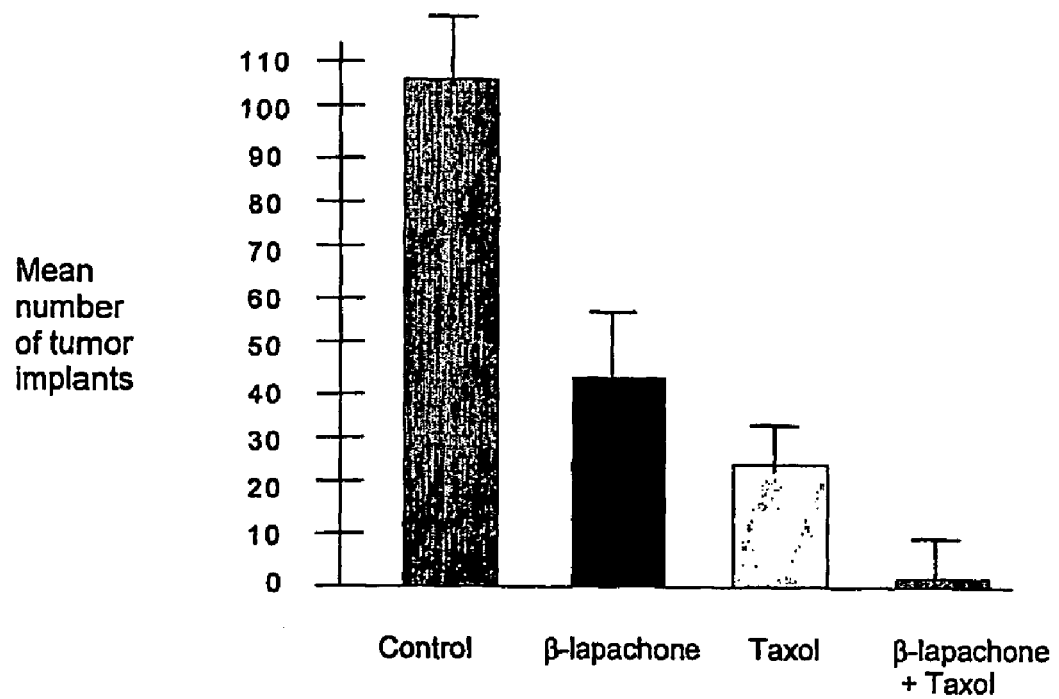
FIG. 9 is a bar graph illustrating the synergistic effect of β-lapachone plus Taxol® in mouse model of human ovarian carcinoma.

FIG. 9 shows the representative results for one of three independent therapeutic experiments, each with 6 mice per group. The decrease in tumor number versus control was quite pronounced with β-lapachone alone (~75%). Mice treated with Taxol® alone showed a slightly smaller effect (~60%), and both groups showed considerable reduction in the size of the tumor nodules and the amount of ascites. In animals treated with β-lapachone plus Taxol®, no malignant ascites were seen on the laparotomy, and the peritoneum was clean except for zero to three tiny foci per mouse. These foci were counted as tumor nodules although they appeared to be fibrotic scars. Mice treated with the combination regimen appeared healthy and did not lose body weight throughout the treatment period, and no gross abnormalities in the internal organs were noted in the autopsy.

A similar study in the human ovarian xenograft model was performed comparing β-lapachone in HPBCD solution with β-lapachone in Lipiodol solution. As with the previous study, treatment was initiated ten days after IP inoculation of $10 \times 10^6$ 36M2 human ovarian cancer cells into athymic female nude mice, 8 per group (animals were not irradiated prior to tumor inoculation). The control group was treated with vehicle alone. In each typical treatment cycle, β-lapachone alone groups received 25 or 10 mg/kg i.p. of β-lapachone in HPBCD solution and the Taxol® alone groups was treated at 1 mg/kg i.p. (Taxol formulation diluted in Lipiodol), both followed 24 h later by i.p. injection of vehicle. In two combination groups, mice were treated with β-lapachone in HPBCD at either 25 or 10 mg/kg, followed 24 h later by Taxol® at 1 mg/kg. A third combination group received β-lapachone in Lipiodol at 25 mg/kg, followed 24 h later by Taxol® at 1 mg/kg. All groups were treated for 6 cycles, with a 1-day break between each cycle. Mice were sacrificed on about Day 50 (about 4 weeks after last treatment) for assessment of antitumor activity.

Figure 10:
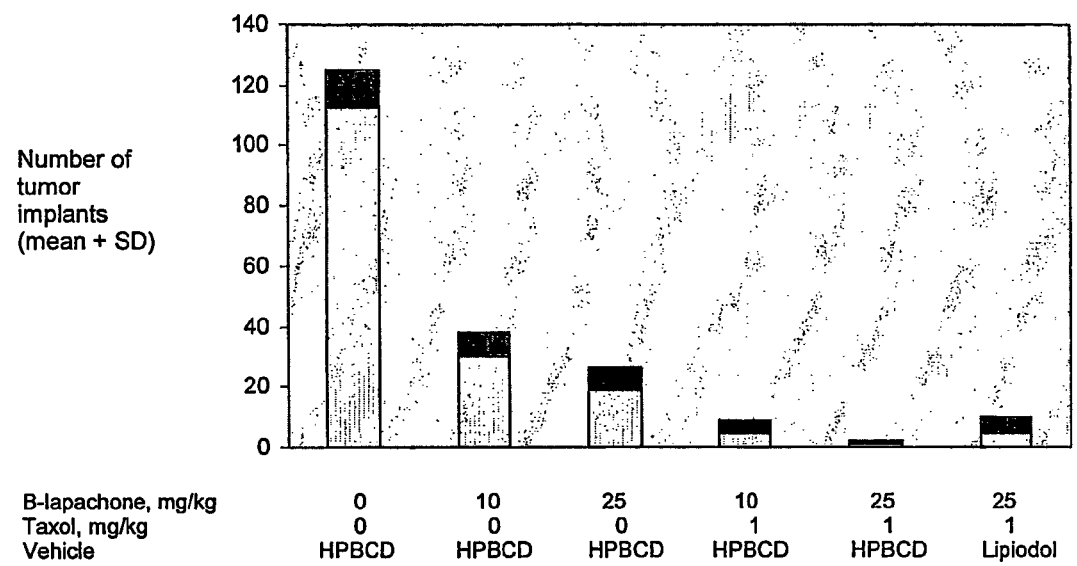
FIG. 10 is a bar graph illustrating that β-lapachone is equally efficacious in the mouse model of human ovarian carcinoma when formulated in HPBCD solution.

FIG. 10 shows the results of this study. Mice treated with β-lapachone in HPBCD solution showed the same reduction in tumor nodules as mice treated with a comparable level of β-lapachone in Lipiodol solution.

Figure 11:
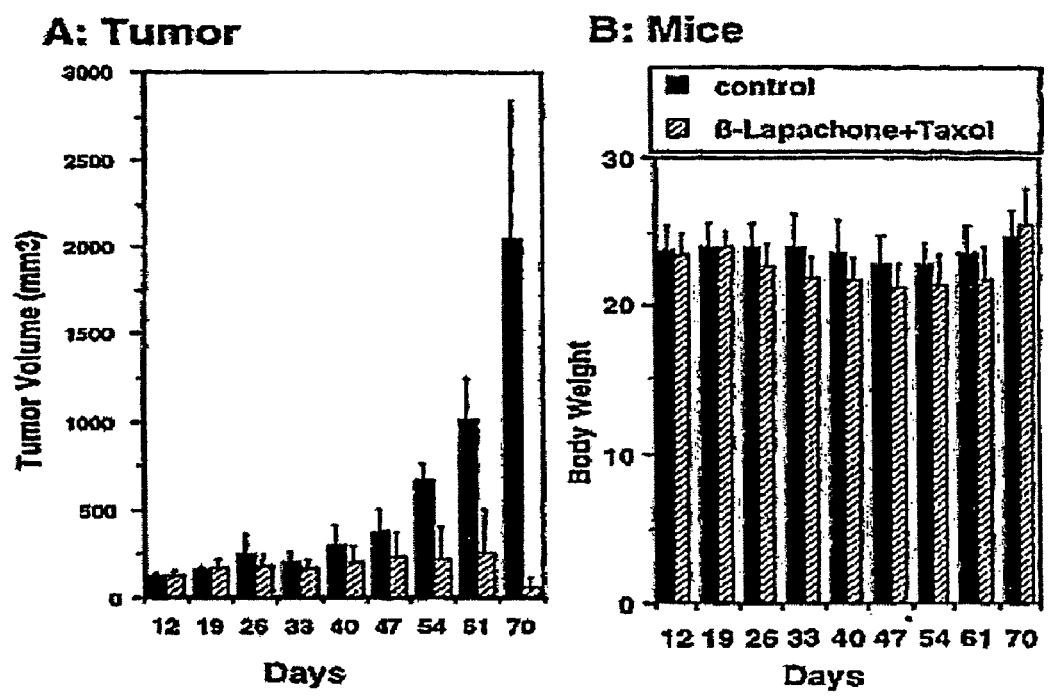
FIG. 11 illustrates anti-tumor activity of β-lapachone and Taxol® in human breast cancer xenograft model.

Potent anti-tumor activity was also demonstrated in female nude mice bearing human breast cancer xenografts (MCF-7 cell line). Treatment of mice was initiated after subcutaneous tumor nodules reached ~0.5 cm in diameter. As shown in FIG. 11, mice receiving six cycles of β-lapachone (50 mg/kg i.p. in Lipiodol solution) and Taxol® (1 mg/kg i.p., 24 h after β-lapachone dose) showed dramatic reduction of tumor volume compared to controls. Furthermore, tumors in the treated mice did not increase in size as of the follow-up. In FIG. 11, the volume of subcutaneous tumor xenograft is shown in chart A and the body weight of the mice measured for 6 weeks after cessation of treatment is shown in chart B.

5. Study of β-lapachone Formulation in Intralipid®

A 10 mg/ml concentrate of β-lapachone in ethanol was prepared. The concentrate was diluted 5×to provide 100-500 μl total. A 2 mg/ml concentration of β-lapachone was prepared in 10% Intralipid® by dropwise addition of the ethanolic solution to the Intralipid® with vortexing. No immediate evidence of precipitation or emulsion breaking was observed.

This procedure was repeated wherein the concentrate was diluted 10× to prepare 1 mg/ml β-lapachone in 10% Intralipid®. Ethanol solution was added dropwise to the Intralipid® with vortexing. No immediate evidence of precipitation or emulsion breaking was observed. After 3 days, the 2 mg/ml preparation had crystals, and the 1 mg/ml preparation showed no changes. After 6 days, the 1 mg/ml preparation still showed no changes.

6. Single Agent β-lapachone Analog Inhibition

Several preferred β-lapachone analogs and derivatives in accordance with the present invention as well as a dunnione analog and 4-hexanoyloxy-1,2-naphthoquinone (as stated infra, see illustrations in FIG. 12) were evaluated for their growth inhibitory activity as compared to β-lapachone (CO-501) in six human cancer cells lines: A2780 and A2780/CP (ovarian); MCF-7 (breast); HT-29 (colon); BxPC-3 (pancreas); and A549 (lung). The human tumor cell lines (purchased from ATCC, Rockville, Md.) were cultured at 37° C. (5% $CO_2$) in RPMI medium (RPMI; Nova Tech, Grand Island, N.Y.) containing 10% fetal bovine serum (FBS, Nova Tech). Aliquots of cells were seeded into each well of 96-well microtiter plates at a final concentration of $10^4$ cells/well and incubated for 24 h prior to exposure to test compounds. Growth inhibitory activity of DMSO solutions of each compound were measured by the MTS assay after 4 hours of treatment followed by 24-hour incubation with drug-free medium. The MTS assay is a colorimetric assay based upon the ability of viable cells to convert MTS, a novel tetrazolium compound and electron-coupling reagent, to a colored formazan product that is soluble in cell culture medium. The cell concentration is then determined by measuring the absorbance of the formazan product at 490 nm. Growth inhibition, expressed as $IC_{50}$, is calculated relative to vehicle-treated control cells. The results of 3 individual assays, each of which involved 3 replicates for each dose level, are shown in Table 9, below.

As expected, a dose-dependent inhibitory effect was observed for β-lapachone (CO-501) in all six tumor cell lines. The dunnione analog (CO-506) showed an activity profile similar to CO-501, as was predicted from the literature. Of the three β-lapachone analogs and derivatives, CO-504 (4-acetoxy β-lapachone) also was very similar to CO-501 in inhibitory activity; CO-503 (4-hydroxy β-lapachone) was significantly less active across all cell lines; and CO505 was inactive (no growth inhibition observed at concentrations as high as 20 μM). CO-507, a naphthoquinone derivative, was also inactive.

TABLE 9

Growth inhibitory activity of β-lapachone (CO-501) and five analogs and derivatives Growth inhibitory activity
(50% effective concentration, $IC_{50}$, expressed as μM)

| Cell Line | CO-501 | CO-503 | CO-504 | CO-505 | CO-506 | CO-507 |
|---|---|---|---|---|---|---|
| Ovarian A2780 (sensitive) | | | | | | |
| Exp 1 | 2.11 | 2.35 | 1.83 | * | 2.47 | * |
| Exp 2 | 3.99 | 5.29 | 1.60 | * | 4.79 | * |
| Exp 3 | 0.876 | 4.857 | 1.19 | * | 3.23 | * |
| Mean ± SE | 2.32 ± 0.91 | 4.16 ± 0.92 | 1.54 ± 0.19 | * | 3.50 ± 0.68 | * |
| Ovarian A2780CP (resistant) | | | | | | |
| Exp 1 | 4.47 | 7.42 | 0.678 | * | 2.73 | * |
| Exp 2 | 1.61 | 9.38 | 4.00 | * | 3.85 | * |
| Exp 3 | 1.76 | 14.8 | 2.56 | * | 1.53 | * |
| Mean ± SE | 2.61 ± 0.93 | 10.5 ± 2.2 | 2.41 ± 0.96 | * | 2.70 ± 0.67 | * |
| Breast MCF-7 | | | | | | |
| Exp 1 | 2.37 | 18.8 | 2.59 | * | 2.64 | * |
| Exp 2 | 4.75 | 19.4 | 4.78 | * | 3.99 | * |
| Exp 3 | 2.10 | 19.3 | 4.28 | * | 3.53 | * |
| Mean ± SE | 3.07 ± 0.84 | 19.2 ± 0.17 | 3.88 ± 0.67 | * | 3.39 ± 0.40 | * |
| Colon HT-29 | | | | | | |
| Exp 1 | 5.37 | 13.2 | 14.1 | * | 17.3 | * |
| Exp 2 | 11.4 | 11.0 | 6.67 | * | 13.4 | * |
| Exp 3 | 9.89 | 12.1 | 3.98 | * | 11.2 | * |
| Mean ± SE | 8.89 ± 1.82 | 12.1 ± 0.63 | 8.25 ± 3.03 | * | 14.0 ± 1.78 | * |
| Pancreas BxPC-3 | | | | | | |
| Exp 1 | 11.6 | * | 10.5 | * | 5.69 | * |

TABLE 9-continued

Growth inhibitory activity of β-lapachone (CO-501) and five analogs and derivatives

| Cell Line | Growth inhibitory activity (50% effective concentration, IC$_{50}$, expressed as μM) | | | | | |
|---|---|---|---|---|---|---|
| | CO-501 | CO-503 | CO-504 | CO-505 | CO-506 | CO-507 |
| Exp 2 | 5.68 | * | 13.5 | * | 8.40 | * |
| Exp 3 | 16.5 | * | 2.32 | * | 9.22 | * |
| Mean ± SE | 11.3 ± 3.12 | * | 8.74 ± 3.33 | * | 7.77 ± 1.07 | * |
| Lung A549 | | | | | | |
| Exp 1 | 4.48 | 14.3 | 19.3 | * | 7.50 | * |
| Exp 2 | 4.73 | 7.63 | 6.87 | * | 12.7 | * |
| Exp 3 | 18.7 | 9.77 | 3.75 | * | 15.3 | * |
| Mean ± SE | 9.30 ± 4.69 | 10.6 ± 1.98 | 9.97 ± 4.74 | * | 11.8 ± 2.28 | * |

*No growth inhibition at up to 20 μM

7. In vivo Testing of β-lapachone in Bg-Nu-Xid Mice

Chemicals. β-lapachone was synthesized and dissolved in 40% hydroxypropyl β-cyclodextrin at a concentration of 10 mg/mL and kept at room temperature in a dark container. Hydroxypropyl β-cyclodextrin was dissolved in distilled water at a concentration of 10 mg/mL and kept at room temperature. MATRIGEL®, a basement membrane matrix was purchased from Becton Dickinson Labware (BD Biosciences, Two Oak Park Drive, Bedford, Mass.) and was dissolved in Dulbecco's modified Eagle's medium with 50 μg/mL Gentamycin and kept frozen at −20° C. MATRIGEL® is extracted from the Engelbreth-Holm-Swarm mouse tumor, a tumor rich in extracellular matrix proteins. The major matrix components are laminin, collagen IV, entactin, and heparan sulfate proteoglycan (perlecan); the matrix also contains growth factors, matrix metalloproteinases (MMPs [collagenases]), and plasminogen activators, without any inhibitors of metalloproteinases (TIMPs). The MATRIGEL matrix is a solution at 4° C. and gels at room temperature to form a three-dimensional reconstituted basement membrane. This model system closely mimics the structure, composition, physical properties, and functional characteristics of the basement membrane in vivo and provides a physiologically relevant environment for studies of cell morphology, biochemical function, migration or invasion, and gene expression. The frozen MATRIGEL® matrix was thawed overnight at 4° C. before use.

Cell Cultures. RPMI8226 cells (a human multiple myeloma cell line) were provided Dr. William Dalton (Lee Moffit Cancer Center, Tampa, Fla.). They were maintained by frequent passages in RPMI 1640 (Cellgro®, Mediatech Inc., Herndon, Va.) containing 10% Fetal Bovine serum (FBS) (GibcoBRL, Life Technologies, Grand Island, N.Y.) supplemented with 2×10$^{-3}$M L-Glutamine, 100 units/mL penicillin (Pen), and 100 μg/mL streptomycin (Cellgro®D, Mediatech Inc., Herndon, Va.) in 162 cm$^2$ cell culture flasks (Costar®, Corning Incorporated, Corning, N.Y.). The exponentially growing cell lines were CD138+, CD38+/CD45RA−, EBV negative, and pathogen free.

Mice. Forty male 6 week old Bg-Nu-Xid mice (deficient in T, B, and NK cells) were obtained from the FCRDC, Frederick, Bethesda, Md. and housed at the Redstone animal facility at DFCI. These mice have 3 separate mutations—Beige (Bg) autosomal recessive mutation associated with impaired chemotaxis and motility of macrophages & deficiency of NK cells; the nude (nu) autosomal recessive mutation associated with depletion of T cells due to thymic agenesis; and the X-linked immune defect (xid) which produces functional defects of B lymphocytes. The animals were raised in a barrier facility in cages with saw dust bedding and laminar air at 19–22° C. Rodent food and sterile drinking water were supplied ad libitum. The mice were quarantined to rule out development of any disease. One mouse died during transport, and 5 others were lost because of dehydration (n=2), probable infection (n=2) and excessive bleeding due to trauma (n=1). After 1 week, enrofloxacin (a quinolone antibiotic) was added in drinking water of all mice. All procedures involving animals were approved by and performed according to guidelines of the Institutional Animal Care and Use Committee of the Dana Farber Cancer Institute (DFCI).

Histologic Analysis. The mice were sacrificed when the tumor reached 20 mm in their largest diameter or they became moribund, as per the policy of the Animal Protocol Committee at Dana Farber Cancer Institute. The mice were anesthetized with isoflurane, and retroorbital blood was collected. The mice were sacrificed by cervical dislocation. The tumors were dissected from the soft tissue (fascia, muscle, skin, etc.) and were fixed in 10% neutralized formalin. Liver, spleen, kidneys, lung, heart and brain from each group were also removed and fixed in formalin. The tissues were dehydrated and embedded in paraffin blocks. They were sectioned into slices 5 μm thick, stained with hematoxylin and eosin (HE), and examined by light microscopy for evidence of apoptosis.

Statistical Analysis. Statistical analysis was done using the student's 't' test for comparing the differences in tumor volumes and degree of apoptosis between lapachone and control groups. p value of <0.05 was considered significant.

Design Thirty four mice were included in the study. RPMI 8226 (3×10$^7$) multiple myeloma cells were washed 3 times, re-suspended in 100 μL RPMI 1640, and injected subcutaneously in the right flank of all mice along with 100 μL of MATRIGEL® matrix using a hypodermic 27G needle and 1 mL syringe. The mice were observed for well being and development of tumors daily, and were weighed weekly.

Figure 13:
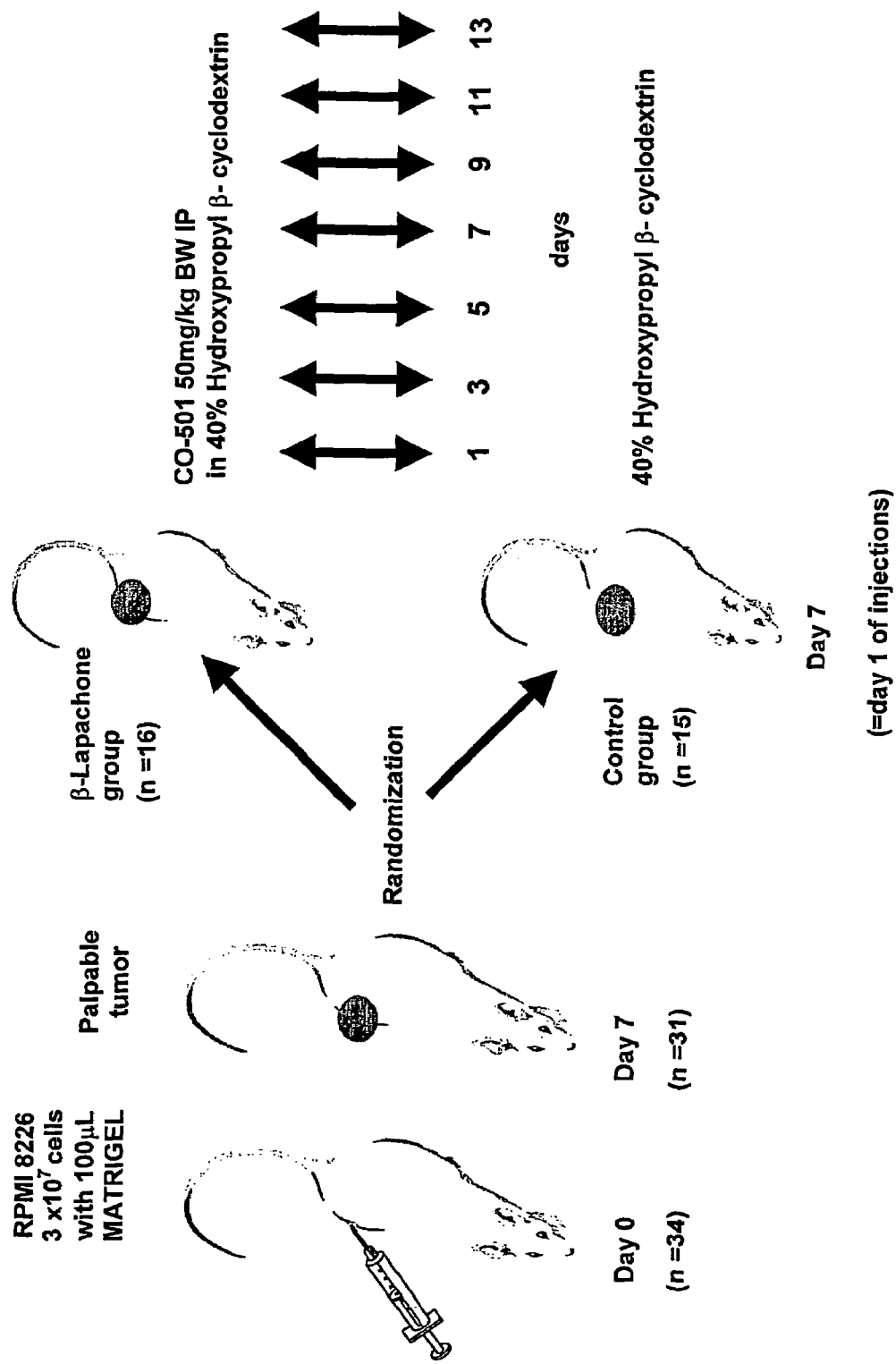
FIG. 13 is a schematic illustrating the injection of RPMI 8226 MM cells and the resulting tumor formation in Bg-Nu-Xid mice.

Localized palpable tumors developed in all mice (n=34) by a mean of 7 days after injection of RPMI 8226 cells. Once the tumors were palpable, they were measured by hand held vernier calipers in 2 orthogonal diameters every other day. Thirty-one mice were randomized to β-lapachone (n=16) and control (n=15) groups. The mice in the control group received 50 mg/kg body weight of 40% hydroxypropyl β-cyclodextrin solution intraperitoneally at the lower left abdominal area every other day. The mice in the β-lapachone group received β-lapachone in 40% hydroxypropyl β-cyclodextrin at 50 mg/kg body weight intraperitoneally every alternate day (FIG. 13). The usual volume at each injection was 125 μL. The diameters of the tumors were recorded, and the volumes were calculated using standard formula for cylindrical objects i.e. 0.523×(Smaller diameter)$^2$×Larger diameter. Mice were sacrificed when the tumor was >20 mm in largest diameter or they became moribund.

This xenograft mouse model is attractive because it is easily established, allows monitoring growth of subcutaneous tumors by external measurements, and can be used to study the effects of various chemotherapeutic agents. Rapidly growing tumors may show some areas of apoptosis/necrosis, but in our experience that has not been a major obstacle in the evaluation of cytotoxicity of various novel potential therapeutic agents. Similar models have been reported previously using anti-gp130 agonist monoclonal antibodies (B1+I2) to study growth and immortalization of multiple myeloma patient cells (Reme et al. Br J Haematol 114:406, 2001) and using anti-human IL-6R antibody PM1 and anti human IL-6 antibody MH166, to inhibit growth of IL-6 dependent cell line (S6B45) (Suzuki et al. Eur J Immunol 22:1989, 1992). Various animal models for testing multiple myeloma therapeutic agents have been reported previously (Gado et al. Haematologica 86: 227, 2001; Dallas et al. Blood 93:1697, 1999; Manning et al. Immunol Cell Biol 73:326, 1995; Takura et al. Cancer Res 26:2564, 1996; Potter et al. J Exp Med 161:996, 1985; Yaccoby et al. Blood 92:2908, 1998; Urashima et al. Blood 90:754, 1997).

Figure 14:
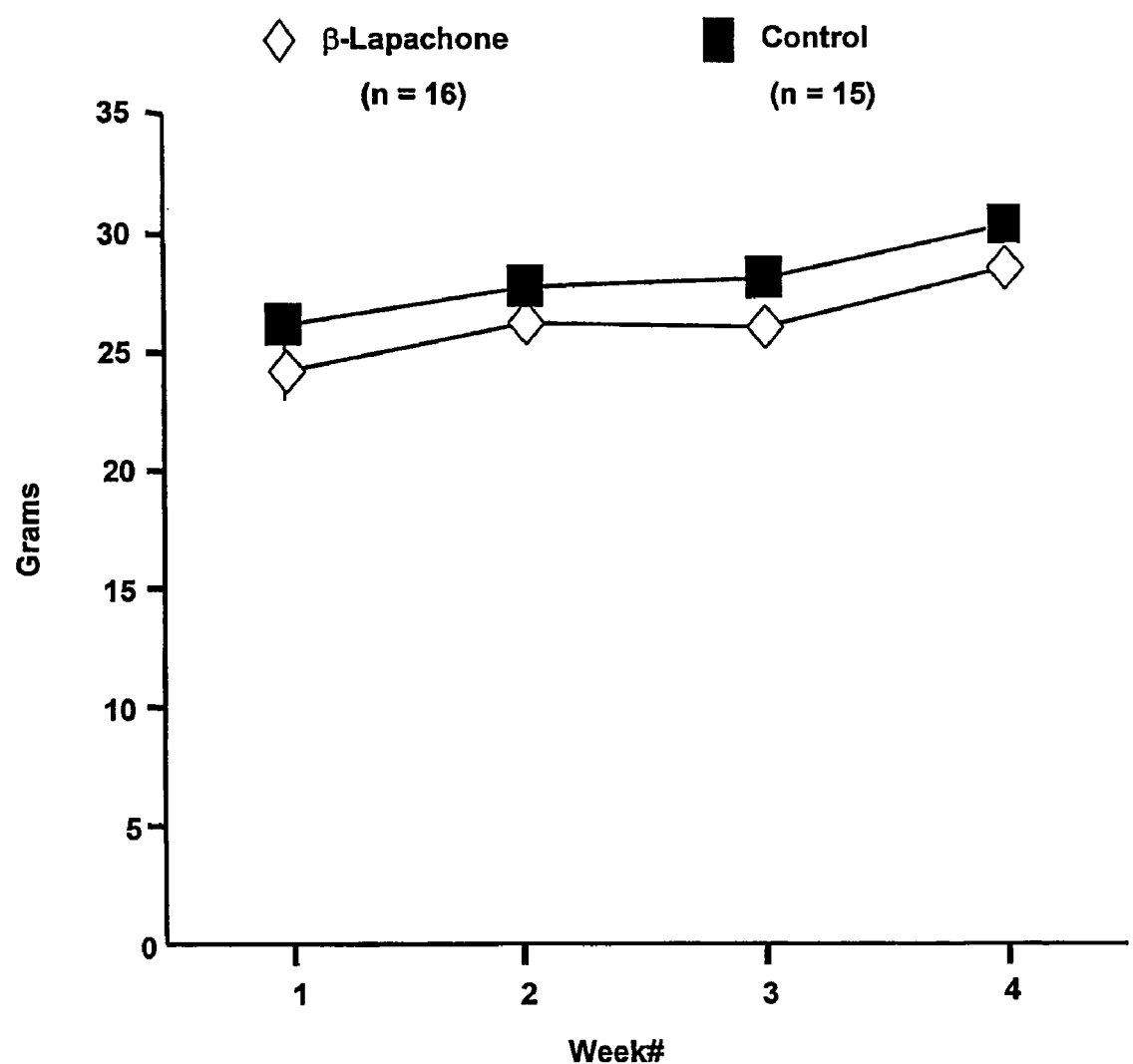
FIG. 14 is a graph showing the average weight pattern of mice during the study.

Determination of β-lapachone and cyclodextrin toxicity. Mice in both groups tolerated β-lapachone and hydroxypropyl β-cyclodextrin well. No mice died in either group and all gained weight (FIG. 14). There was no evidence of overt toxicity of β-lapachone or hydroxypropyl β-cyclodextrin in either cohort. One mouse developed iatrogenic intra-peritoneal hemorrhage after injection of β-lapachone which resolved in 36 h. Mild tubular vacuolization of kidneys in both β-lapachone and control groups was also found. Since this effect was present in both groups, hydroxypropyl β-cyclodextrin is implicated, as has been previously reported for cyclodextrins (Frank et al. Am J Pathol 83:367, 1976) and these nephrotoxic changes are reversible with cessation of treatment (Donaubauer et al. Regul Toxicol Pharmacol 27:189, 1998).

Figure 15:
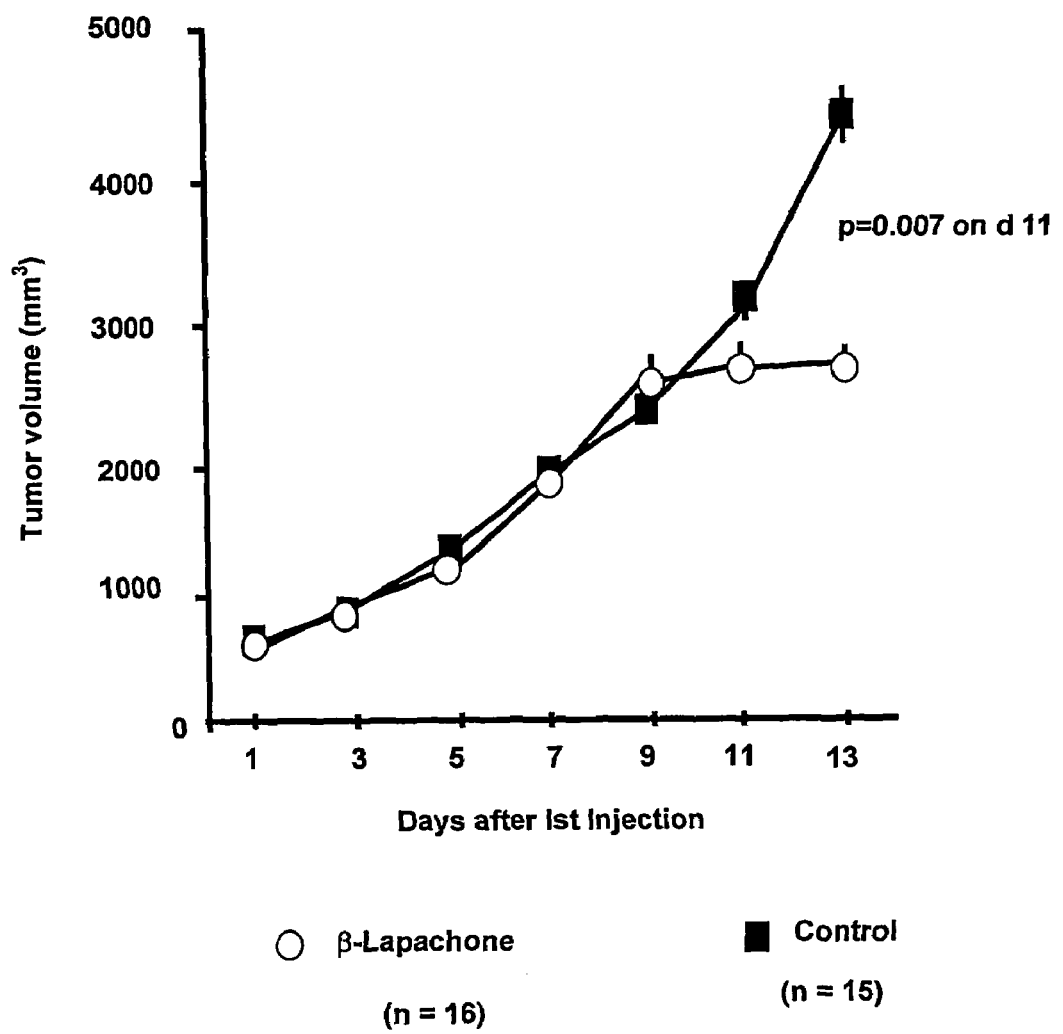
FIG. 15 is a graph showing the effect on β-lapachone/Hydroxypropyl β-cyclodextrin on tumor volume.
Figure 16:
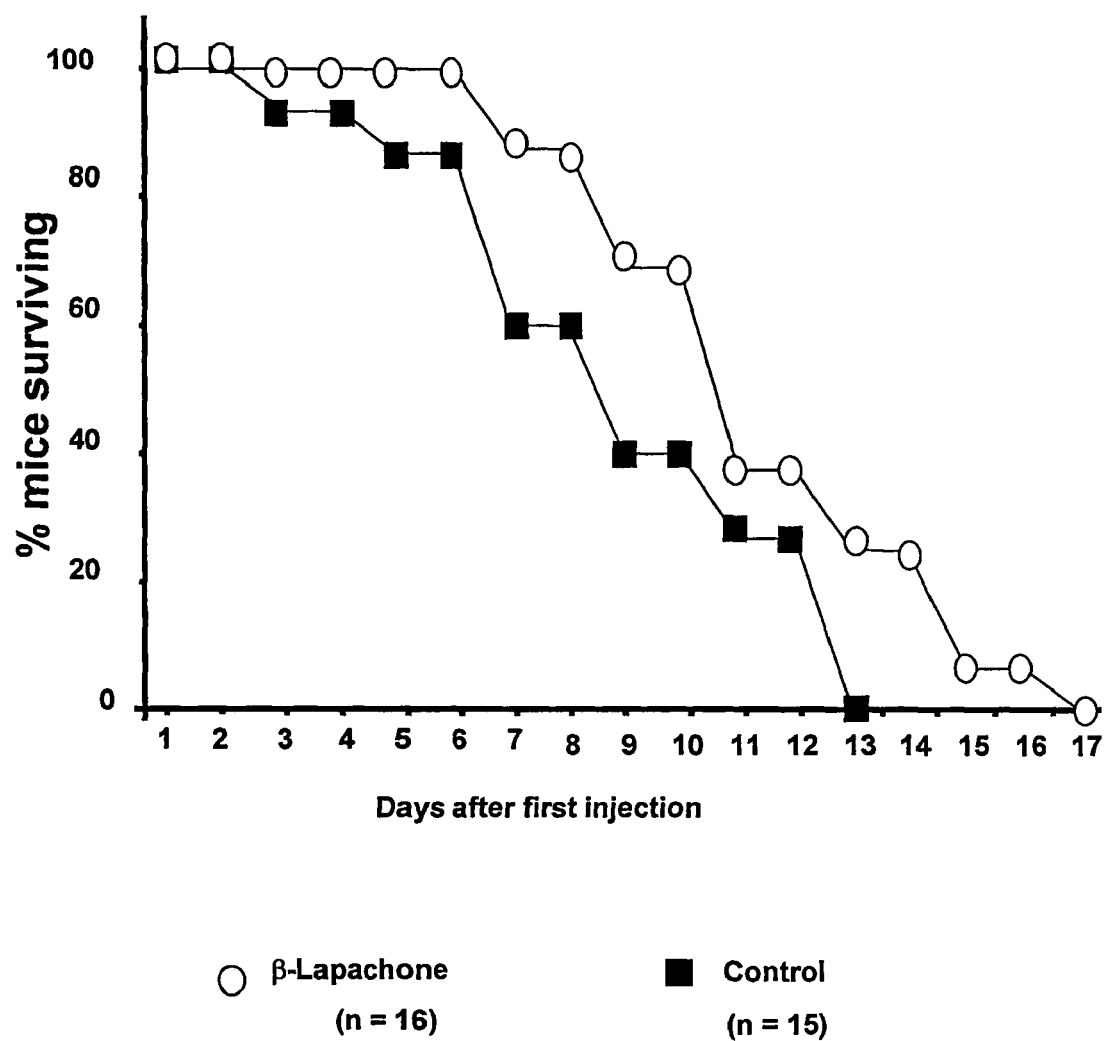
FIG. 16 is a graph showing the effect of β-lapachone/hydroxypropyl β-cyclodextrin on the survival of mice in both groups.

Effects on β-lapachone tumor volume. Mice in control group received a maximum of 6 doses of hydroxypropyl β-cyclodextrin, whereas the mice in the β-lapachone group were able to receive a maximum of 8 doses of this agent. There was a statistically significant decrease in tumor volume of mice in β-lapachone group (p=0.007) versus control group (FIG. 15) by day 11. Importantly, survival was greater at day 5, 7, 9, 11, 13, 15 and 17 in the β-lapachone group compared to controls (FIG. 16), suggestive of slower tumor growth in β-lapachone group.

Histologic Staining. Histopathologic examination revealed that tumors were not encapsulated and were locally invasive to soft tissues, including muscle, without any distant metastasis. Tumors were vascularized by blood vessels of murine origin, with a minor variable degree (0–10%) of cell death primarily in their cores. Apoptosis was assessed histopathologically on the basis of (1) chromatin condensation and aggregation near the nuclear membrane with convolution of the nuclear membrane; (2) enlarged and abnormally granular nucleolus; (3) shrinkage and rounding of cells; (4) blebbing of cell membranes; and (5) minor dilation of endoplasmic reticulum and mitochondria There was a statistically significant increase in MM cell apoptosis (p=0.001) in tumors in the β-lapachone (mean±SD= 41.1%±12.7) versus control (mean±SD=20.0%±10.4) groups, as assessed by two blinded independent observers using light microscopy (FIG. 17A).

Figure 17:
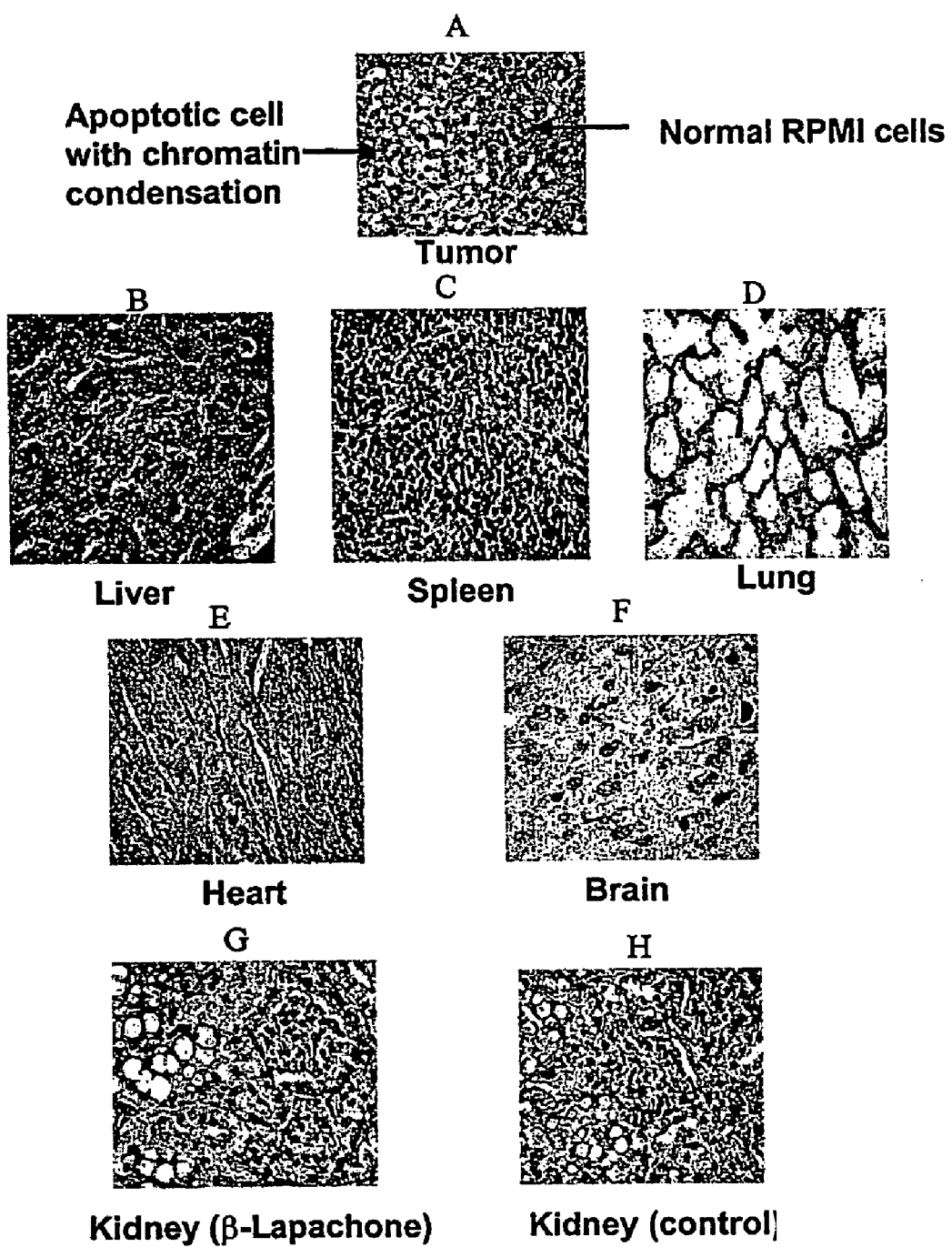
FIG. 17 illustrates representative photomicrographs showing the effect of β-lapachone/hydroxypropyl β-cyclodextrin on tumors, as well as liver, spleen, lung, heart, brain and kidneys.

There was no microscopic evidence of any toxicity of β-lapachone or hydroxypropyl β-cyclodextrin on liver, heart, lung, brain, and spleen in mice in either β-lapachone or control groups (FIG. 17B, C, D, E, F). Kidneys from mice in both groups showed mild tubular vacuolization, suggesting tubular toxicity of hydroxypropyl β-cyclodextrin (FIG. 17G, H). This toxicity is not expected to be seen at the anticipated treatment doses in humans based on with previous drugs formulated in HPBCD. These results indicate that β-lapachone, formulated in HPBCD, is safe and effective at inhibiting tumor cell growth, associated with prolonged host survival in vivo. Thus it can be concluded that beta lap has significant anti-tumor activity with minimal toxicity and can be used to treat multiple myeloma in vivo.

EQUIVALENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The claims presented are representative of the inventions disclosed herein. Other, unclaimed inventions are also contemplated. It is to be understood that the drawings are not necessarily drawn to scale, but that they are merely conceptual in nature. Applicants reserve the right to pursue such inventions in later claims.

What is claimed is:

1. A method for treating cancer comprising administering to a patient a pharmaceutical composition comprising a therapeutically effective amount of Beta-lapachone, or a derivative or analog thereof, and a pharmaceutically acceptable solubilizing carrier molecule, wherein said cancer is selected from the group consisting of multiple myeloma, ovary, breast, melanoma, colon, pancreas, lung and prostate and wherein said solubilizing carrier molecule is a beta-cyclodextrin.

2. The method of claim 1, wherein the pharmaceutical composition when diluted with an aqueous solution for parenteral administration, remains soluble in the aqueous solution.

3. The method of claim 2, wherein the pharmaceutical composition comprises a complex or solution of the therapeutically effective amount of Beta-lapachone, or a derivative or analog thereof, and the pharmaceutically acceptable solubilizing carrier molecule.

4. A method for treating cancer comprising administering to a patient a formulation of Beta-lapachone, or a derivative or analog thereof, and a pharmaceutically acceptable solubilizing carrier molecule, wherein the complex can be freeze-dried and when subsequently reconstituted in aqueous solution is soluble, wherein said cancer is selected from the group consisting of multiple myeloma, ovary, breast, melanoma, colon, pancreas, lung and prostate and wherein said solubilizing carrier molecule is a beta-cyclodextrin.

5. The method of claim 4, wherein the formulation comprises a complex or solution of the Beta-lapachone, or a derivative or analog thereof, and the pharmaceutically acceptable solubilizing carrier molecule.

6. The method of claim 4, wherein the formulation is administered parenterally.

7. The method of claim 6, wherein said formulation comprises a dosage unit in the range between 0.1 mg/kg to 10 mg/kg administered from between twice weekly to once every four weeks.

8. A method for treating cancer comprising administering to a patient a pharmaceutical composition comprising a therapeutically effective amount of Beta-lapachone, or a derivative or analog thereof and a pharmaceutically acceptable solubilizing carrier molecule, and further comprising a second anticancer agent and a pharmaceutically acceptable carrier, wherein said cancer is selected from the group consisting of multiple myeloma, ovary, breast, melanoma, colon, pancreas, lung and prostate and wherein said solubilizing carrier molecule is a beta-cyclodextrin.

9. The method of claim 8, wherein the pharmaceutical composition comprises a complex or solution of the therapeutically effective amount of Beta-lapachone, or a derivative or analog thereof, and the pharmaceutically acceptable solubilizing carrier molecule, and further comprising the second anticancer agent and a pharmaceutically acceptable carrier.

10. The method of claim 8, wherein the second anticancer agent is a taxane derivative.

11. The method of claim 10, wherein the taxane derivative is paclitaxel.

12. The method of claim 8, wherein the pharmaceutical composition is administered parenterally.

13. The method of claim 8, wherein the pharmaceutical composition when diluted with an aqueous solution for parenteral administration, remains soluble in the aqueous solution.

14. The method of claim 13, wherein the pharmaceutical composition comprises a complex or solution of the therapeutically effective amount of Beta-lapachone, or a derivative or analog thereof and the pharmaceutically acceptable solubilizing carrier molecule, which when diluted with the aqueous solution for parenteral administration, remains soluble in the aqueous solution.

15. A method for treating cancer comprising administering to a patient a formulation of Beta-lapachone, or a derivative or analog thereof, and a pharmaceutically acceptable solubilizing carrier molecule, wherein the formulation can be freeze-dried and when subsequently reconstituted in aqueous solution is soluble and further comprising a second anticancer agent and a pharmaceutically acceptable carrier, wherein said cancer is selected from the group consisting of multiple myeloma, ovary, breast, melanoma, colon, pancreas, lung and prostate and wherein said solubilizing carrier molecule is a beta-cyclodextrin.

16. The method of claim 15, wherein the formulation comprises a complex or solution of the Beta-lapachone, or a derivative or analog thereof, and the pharmaceutically acceptable solubilizing carrier molecule, and further comprising the second anticancer agent and a pharmaceutically acceptable carrier.

17. A method for treating cancer comprising first administering to a patient a pharmaceutical composition comprising a therapeutically effective amount of Beta-lapachone, or a derivative or analog thereof, and a pharmaceutically acceptable solubilizing carrier molecule, and subsequently subjecting said patient to radiation therapy, wherein said cancer is selected from the group consisting of multiple myeloma, ovary, breast, melanoma, colon, pancreas, lung and prostate and wherein said solubilizing carrier molecule is a beta-cyclodextrin.

18. A method for treating skin cancer or a dermatologic condition comprising administering to a patient a therapeutically effective amount of a pharmaceutical composition comprising a therapeutically effective amount of a Beta-Lapachone, or a derivative or analog thereof, and a pharmaceutically acceptable solubilizing carrier molecule, wherein said solubilizing carrier molecule is a beta-cyclodextrin.

19. The method of claim 18, wherein the pharmaceutical composition is administered topically.

20. The method of claim 1, wherein the pharmaceutical composition is administered parenterally.

21. The method of claim 1, wherein the pharmaceutical composition comprises a complex or solution of the therapeutically effective amount of Beta-lapachone, or a derivative or analog thereof, and the pharmaceutically acceptable solubilizing carrier molecule, which when diluted with the aqueous solution for parenteral administration, remains soluble in the aqueous solution.

22. The method of claim 17, wherein the pharmaceutical composition when diluted with an aqueous solution for parenteral administration, remains soluble in the aqueous solution.

23. The method of claim 17, wherein the pharmaceutical composition comprises a complex or solution of the therapeutically effective amount of Beta-lapachone, or a derivative or analog thereof, and the pharmaceutically acceptable solubilizing carrier molecule, and further comprising the second anticancer agent and a pharmaceutically acceptable carrier.

24. The method of claim 18, wherein the pharmaceutical composition comprises a complex or solution of the therapeutically effective amount of Beta-lapachone, or a derivative or analog thereof, and the pharmaceutically acceptable solubilizing carrier molecule, and further comprising the second anticancer agent and a pharmaceutically acceptable carrier.

25. The method of claim 15, wherein the pharmaceutical composition is administered parenterally.

26. The method of claim 17, wherein the pharmaceutical composition is administered parenterally.

27. The method of claim 17, wherein the pharmaceutical composition comprises a complex or solution of the therapeutically effective amount of Beta-lapachone, or a derivative or analog thereof and the pharmaceutically acceptable solubilizing carrier molecule, which when diluted with the aqueous solution for parenteral administration, remains soluble in the aqueous solution.

28. The method of claim 1, wherein said pharmaceutical composition comprises a dosage unit in the range between 0.1 mg/kg to 10 mg/kg administered from between twice weekly to once every four weeks.

29. The method of claim 8, wherein said pharmaceutical composition comprises a dosage unit in the range between 0.1 mg/kg to 10 mg/kg administered from between twice weekly to once every four weeks.

30. The method of claim 15, wherein said formulation comprises a dosage unit in the range between 0.1 mg/kg to 10 mg/kg administered from between twice weekly to once every four weeks.

31. The method of claim 17, wherein said pharmaceutical composition comprises a dosage unit in the range between 0.1 mg/kg to 10 mg/kg administered from between twice weekly to once every four weeks.

32. The method of claim 18, wherein said pharmaceutical composition comprises a dosage unit in the range between 0.1 mg/kg to 10 mg/kg administered from between twice weekly to once every four weeks.

33. The method of claim 15, wherein the second anticancer agent is a taxane derivative.

34. The method of claim 33, wherein the taxane derivative is paclitaxel.

* * * * *